(12) United States Patent
Patton et al.

(10) Patent No.: US 7,521,069 B2
(45) Date of Patent: *Apr. 21, 2009

(54) METHODS AND COMPOSITIONS FOR PULMONARY DELIVERY OF INSULIN

(75) Inventors: John S. Patton, Portola Valley, CA (US); Linda S. Foster, Sunnyvale, CA (US); Robert M. Platz, Half Moon Bay, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/612,376

(22) Filed: Jul. 1, 2003

(65) Prior Publication Data

US 2004/0096400 A1 May 20, 2004

Related U.S. Application Data

(60) Continuation of application No. 08/668,036, filed on Jun. 17, 1996, now Pat. No. 6,685,967, which is a division of application No. 08/383,475, filed on Feb. 1, 1995, now abandoned, which is a continuation-in-part of application No. 08/207,472, filed on Mar. 7, 1994, now abandoned.

(51) Int. Cl.
*A61K 9/14* (2006.01)
*A61K 9/12* (2006.01)
*A61K 38/28* (2006.01)

(52) U.S. Cl. .......................... 424/499; 424/43; 424/45; 424/489; 514/3; 514/866

(58) Field of Classification Search ............. 424/43–46, 424/489–502, 434; 514/21, 2, 3, 866, 8; 128/200.14, 200.18
See application file for complete search history.

(56) References Cited

U.S. PATENT DOCUMENTS

| 979,993 | A | 12/1910 | O'Byrne et al. |
| 1,855,591 | A | 4/1932 | Wallenstein |
| 2,598,525 | A | 5/1952 | Fox |
| 3,202,731 | A | 8/1965 | Grevenstuk et al. |
| 3,300,474 | A | 1/1967 | Flodin et al. |
| 3,314,803 | A | 4/1967 | Tarrytown et al. |
| 3,362,405 | A | 1/1968 | Hazel |

(Continued)

FOREIGN PATENT DOCUMENTS

BE 902 257 8/1985

(Continued)

OTHER PUBLICATIONS

Andrews, "Gelatin Capsules Revamped for New Generation of Pills," New York Times, Saturday, Sep. 16, 1992, 19(N), 35(L), col. 5, 9 col. in.

(Continued)

*Primary Examiner*—Gollamudi S Kishore
(74) *Attorney, Agent, or Firm*—John W. Kung; Sandra S. Shim

(57) ABSTRACT

Systemic delivery of insulin to a mammalian host is accomplished by inhalation of a dry powder of insulin. It has been found that dry insulin powders are rapidly absorbed through the alveolar regions of the lungs.

34 Claims, 8 Drawing Sheets

U.S. PATENT DOCUMENTS

| | | |
|---|---|---|
| 3,425,600 A | 2/1969 | Ablanalp |
| 3,540,927 A | 11/1970 | Niimi et al. |
| 3,554,768 A | 1/1971 | Feldman |
| 3,555,717 A | 1/1971 | Chivers |
| 3,619,294 A | 11/1971 | Black et al. |
| 3,620,776 A | 11/1971 | Mishkin et al. |
| 3,632,357 A | 1/1972 | Childs |
| 3,655,442 A | 4/1972 | Schwer et al. |
| 3,666,496 A | 5/1972 | Honey et al. |
| 3,674,901 A | 7/1972 | Shepherd et al. |
| 3,745,682 A | 7/1973 | Waldeisen |
| 3,764,716 A | 10/1973 | Rainwater et al. |
| 3,921,637 A | 11/1975 | Bennie et al. |
| 3,937,668 A | 2/1976 | Zolle |
| 3,948,263 A | 4/1976 | Drake, Jr. et al. |
| 3,964,483 A | 6/1976 | Mathes |
| 3,971,852 A | 7/1976 | Brenner et al. |
| 3,991,304 A | 11/1976 | Hillsman |
| 3,991,761 A | 11/1976 | Cocozza |
| 3,994,421 A | 11/1976 | Hansen |
| 4,036,223 A | 7/1977 | Obert |
| 4,069,819 A | 1/1978 | Valentini et al. |
| 4,098,273 A | 7/1978 | Glenn |
| 4,102,999 A | 7/1978 | Umezawa et al. |
| 4,109,019 A | 8/1978 | Moore |
| 4,127,502 A | 11/1978 | Li Mutti et al. |
| 4,127,622 A | 11/1978 | Watanabe et al. |
| 4,153,689 A | 5/1979 | Hiral et al. |
| 4,158,544 A | 6/1979 | Louderback |
| 4,159,319 A | 6/1979 | Bachmann et al. |
| 4,180,593 A | 12/1979 | Cohan |
| 4,206,200 A | 6/1980 | Guthohrlein et al. |
| 4,211,769 A * | 7/1980 | Okada et al. ............... 514/15 |
| 4,244,949 A | 1/1981 | Gupta |
| 4,249,526 A | 2/1981 | Dean et al. |
| 4,253,468 A | 3/1981 | Lehmbeck |
| 4,294,624 A | 10/1981 | Veltman |
| 4,294,829 A | 10/1981 | Suzuki et al. |
| 4,326,524 A | 4/1982 | Drake, Jr. et al. |
| 4,327,076 A | 4/1982 | Puglia et al. |
| 4,327,077 A | 4/1982 | Puglia et al. |
| 4,338,931 A | 7/1982 | Cavazza |
| 4,371,557 A | 2/1983 | Oppy et al. |
| 4,407,786 A | 10/1983 | Drake et al. |
| 4,423,079 A | 12/1983 | Kline |
| 4,446,862 A | 5/1984 | Baum et al. |
| 4,452,239 A | 6/1984 | Malem |
| 4,484,577 A | 11/1984 | Sackner et al. |
| 4,503,035 A | 3/1985 | Pestka et al. |
| 4,533,552 A | 8/1985 | Kawamata et al. |
| 4,534,343 A | 8/1985 | Nowacki et al. |
| 4,559,298 A | 12/1985 | Fahy |
| 4,588,744 A | 5/1986 | McHugh |
| 4,590,206 A | 5/1986 | Forrester et al. |
| 4,591,552 A | 5/1986 | Neurath |
| 4,599,311 A | 7/1986 | Kawasaki |
| 4,613,500 A | 9/1986 | Suzuki et al. |
| 4,614,730 A | 9/1986 | Hansen |
| 4,617,272 A | 10/1986 | Kirkwood et al. |
| 4,620,847 A | 11/1986 | Shishov et al. |
| 4,624,251 A | 11/1986 | Miller |
| 4,627,432 A | 12/1986 | Newell et al. |
| 4,649,911 A | 3/1987 | Knight et al. |
| 4,659,696 A * | 4/1987 | Hirai et al. ............... 514/15 |
| 4,677,975 A | 7/1987 | Edgar et al. |
| 4,680,027 A | 7/1987 | Parsons et al. |
| 4,684,719 A | 8/1987 | Nishikawa et al. |
| 4,698,328 A | 10/1987 | Neer et al. |
| 4,701,417 A | 10/1987 | Portenhauser et al. |
| 4,713,249 A | 12/1987 | Schroder |
| 4,719,762 A | 1/1988 | Osabe |
| 4,721,709 A | 1/1988 | Seth et al. |
| 4,739,754 A | 4/1988 | Shaner |
| 4,758,583 A | 7/1988 | Cerami et al. |
| 4,761,400 A | 8/1988 | Doat et al. |
| 4,762,857 A | 8/1988 | Bollin, Jr. et al. |
| 4,778,054 A | 10/1988 | Newell et al. |
| 4,790,305 A | 12/1988 | Zoltan et al. |
| 4,790,824 A | 12/1988 | Morrow et al. |
| 4,793,997 A | 12/1988 | Drake et al. |
| 4,806,343 A | 2/1989 | Carpenter et al. |
| 4,807,814 A | 2/1989 | Douche et al. |
| 4,811,731 A | 3/1989 | Newell et al. |
| 4,812,444 A | 3/1989 | Mitsuhashi et al. |
| 4,814,436 A | 3/1989 | Shibata et al. |
| 4,819,629 A | 4/1989 | Jonson |
| 4,820,534 A | 4/1989 | Saleeb et al. |
| 4,823,784 A | 4/1989 | Borkoni et al. |
| 4,824,938 A | 4/1989 | Koyama et al. |
| 4,830,858 A | 5/1989 | Payne et al. |
| 4,833,125 A | 5/1989 | Neer et al. |
| 4,847,079 A | 7/1989 | Kwan |
| 4,855,157 A | 8/1989 | Tashiro et al. |
| 4,855,326 A | 8/1989 | Fuisz |
| 4,857,319 A | 8/1989 | Crowe et al. |
| 4,861,627 A | 8/1989 | Mathiowitz et al. |
| 4,865,871 A | 9/1989 | Livesey et al. |
| 4,866,051 A | 9/1989 | Hunt et al. |
| 4,876,241 A | 10/1989 | Feldman et al. |
| 4,883,762 A | 11/1989 | Hoskins |
| 4,884,565 A | 12/1989 | Cocozza |
| 4,889,114 A | 12/1989 | Kladders |
| 4,891,319 A | 1/1990 | Roser |
| 4,895,719 A | 1/1990 | Radhakrishnan et al. |
| 4,897,353 A | 1/1990 | Carpenter et al. |
| 4,906,463 A | 3/1990 | Cleary et al. |
| 4,907,583 A | 3/1990 | Wetterlin et al. |
| 4,919,962 A | 4/1990 | Arora et al. |
| 4,926,852 A | 5/1990 | Zoltan et al. |
| 4,927,763 A | 5/1990 | Sudoma et al. |
| 4,931,361 A | 6/1990 | Baldeschwieler et al. |
| 4,942,544 A | 7/1990 | McIntosh et al. |
| 4,946,828 A * | 8/1990 | Markussen ............... 514/3 |
| 4,952,402 A | 8/1990 | Sparks et al. |
| 4,956,295 A | 9/1990 | Sudoma |
| 4,968,607 A | 11/1990 | Dower et al. |
| 4,984,158 A | 1/1991 | Hillsman |
| 4,988,683 A | 1/1991 | Corbiere |
| 4,995,385 A | 2/1991 | Valentini et al. |
| 5,006,343 A | 4/1991 | Benson et al. |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Foster |
| 5,026,772 A | 6/1991 | Kobayashi et al. |
| 5,027,806 A | 7/1991 | Zoltan et al. |
| 5,033,463 A | 7/1991 | Cocozza |
| 5,035,237 A | 7/1991 | Newell et al. |
| 5,042,975 A * | 8/1991 | Chien et al. ............... 604/20 |
| 5,043,165 A | 8/1991 | Radhakrishnan |
| 5,048,514 A | 9/1991 | Ramella |
| 5,049,388 A | 9/1991 | Kright et al. |
| 5,049,389 A | 9/1991 | Radhakrishnan |
| 5,059,587 A | 10/1991 | Yamamoto et al. |
| 5,081,228 A | 1/1992 | Dower et al. |
| 5,089,181 A | 2/1992 | Hauser |
| 5,093,316 A | 3/1992 | Lezdey et al. |
| 5,098,893 A | 3/1992 | Franks et al. |
| 5,099,833 A | 3/1992 | Michaels |
| 5,112,596 A | 5/1992 | Malfroy-Caine |
| 5,112,598 A | 5/1992 | Biesalski |
| 5,113,855 A | 5/1992 | Newhouse |
| 5,124,162 A | 6/1992 | Boskovic et al. |
| 5,139,016 A | 8/1992 | Waser |

| | | | | | |
|---|---|---|---|---|---|
| 5,149,543 A | 9/1992 | Cohen et al. | 5,642,728 A | 7/1997 | Andersson et al. |
| 5,149,653 A | 9/1992 | Roser | 5,654,278 A | 8/1997 | Sosrensen |
| 5,160,745 A | 11/1992 | DeLuca et al. | 5,672,581 A | 9/1997 | Rubsamen et al. |
| 5,161,524 A | 11/1992 | Evans | 5,681,746 A | 10/1997 | Bodner et al. |
| 5,173,298 A | 12/1992 | Meadows | 5,705,482 A | 1/1998 | Christensen et al. |
| 5,180,812 A | 1/1993 | Dower et al. | 5,707,352 A | 1/1998 | Sekins |
| 5,182,097 A | 1/1993 | Byron et al. | 5,728,574 A | 3/1998 | Legg |
| 5,186,164 A | 2/1993 | Raghuprasad | 5,733,555 A | 3/1998 | Chu |
| 5,200,399 A | 4/1993 | Wettlaufer et al. | 5,755,221 A | 5/1998 | Bisgaard |
| 5,202,333 A | 4/1993 | Berger et al. | 5,766,520 A | 6/1998 | Bronshtein |
| 5,204,108 A | 4/1993 | Illum | 5,775,320 A | 7/1998 | Patton et al. |
| 5,206,200 A | 4/1993 | Bush et al. | 5,780,014 A | 7/1998 | Eljamal et al. |
| 5,215,079 A | 6/1993 | Fine et al. | 5,780,295 A | 7/1998 | Livesey et al. |
| 5,225,183 A | 7/1993 | Purewal et al. | 5,792,366 A | 8/1998 | Coville |
| 5,230,884 A | 7/1993 | Evans et al. | 5,849,700 A | 12/1998 | Sorensen et al. |
| 5,239,993 A | 8/1993 | Evans | 5,851,453 A | 12/1998 | Hanna et al. |
| 5,240,712 A | 8/1993 | Smith et al. | 5,891,873 A | 4/1999 | Colaco et al. |
| 5,240,843 A | 8/1993 | Gibson et al. | 5,928,469 A | 7/1999 | Franks et al. |
| 5,240,846 A | 8/1993 | Collins et al. | 5,948,411 A | 9/1999 | Koyama et al. |
| 5,253,468 A | 10/1993 | Raymond | 5,955,448 A | 9/1999 | Calaco et al. |
| 5,254,330 A | 10/1993 | Ganderton | 5,976,436 A | 11/1999 | Livesley et al. |
| 5,260,306 A | 11/1993 | Boardman et al. | 5,993,783 A | 11/1999 | Eljamal et al. |
| 5,270,048 A | 12/1993 | Drake | 5,993,805 A | 11/1999 | Sutton et al. |
| 5,284,656 A | 2/1994 | Platz et al. | 5,994,314 A | 11/1999 | Eljamal et al. |
| 5,290,765 A | 3/1994 | Wettlaufer et al. | 5,997,848 A * | 12/1999 | Patton et al. .................. 424/46 |
| 5,295,479 A | 3/1994 | Lankinen | 6,012,454 A | 1/2000 | Hodson et al. |
| 5,302,581 A | 4/1994 | Sarin et al. | 6,013,638 A | 1/2000 | Crystal et al. |
| 5,306,506 A | 4/1994 | Zema et al. | 6,019,968 A | 2/2000 | Platz et al. |
| 5,309,900 A | 5/1994 | Knoch et al. | 6,034,080 A | 3/2000 | Colaco et al. |
| 5,312,335 A | 5/1994 | McKinnon et al. | 6,051,256 A | 4/2000 | Platz et al. |
| 5,312,909 A | 5/1994 | Driessen et al. | 6,060,069 A | 5/2000 | Hill et al. |
| 5,320,094 A | 6/1994 | Laube et al. | 6,071,428 A | 6/2000 | Franks et al. |
| 5,320,714 A | 6/1994 | Brendel | 6,077,543 A | 6/2000 | Gordon et al. |
| 5,331,953 A | 7/1994 | Anderson et al. | 6,099,517 A | 8/2000 | Daugherty |
| 5,342,625 A | 8/1994 | Hauer et al. | 6,123,924 A | 9/2000 | Mistry et al. |
| 5,348,852 A | 9/1994 | Bonderman | 6,123,936 A | 9/2000 | Platz et al. |
| 5,354,562 A * | 10/1994 | Platz et al. ................... 424/489 | 6,136,346 A | 10/2000 | Eljamal et al. |
| 5,354,934 A | 10/1994 | Pitt et al. | 6,138,668 A | 10/2000 | Patton et al. |
| 5,356,635 A | 10/1994 | Raman et al. | 6,142,216 A | 11/2000 | Lannes |
| 5,364,838 A * | 11/1994 | Rubsamen ...................... 514/3 | 6,165,463 A | 12/2000 | Platz et al. |
| 5,366,734 A | 11/1994 | Hutchinson | 6,187,344 B1 | 2/2001 | Eljamal et al. |
| 5,376,359 A | 12/1994 | Johnson | 6,190,859 B1 | 2/2001 | Putnak et al. |
| 5,376,386 A | 12/1994 | Ganderton et al. | 6,231,851 B1 | 5/2001 | Platz et al. |
| 5,380,473 A | 1/1995 | Bogue et al. | 6,258,341 B1 | 7/2001 | Foster et al. |
| 5,384,133 A | 1/1995 | Boyes et al. | 6,290,991 B1 | 9/2001 | Roser et al. |
| 5,387,431 A | 2/1995 | Fuisz | 6,303,581 B2 | 10/2001 | Pearlman |
| 5,403,861 A | 4/1995 | Goldin et al. | 6,303,582 B1 | 10/2001 | Eljamal et al. |
| 5,404,871 A | 4/1995 | Goodman et al. | 6,309,671 B1 | 10/2001 | Foster et al. |
| 5,419,315 A | 5/1995 | Rubsamen | 6,313,102 B1 | 11/2001 | Colaco et al. |
| 5,422,360 A | 6/1995 | Miyajima et al. | 6,331,310 B1 | 12/2001 | Roser et al. |
| 5,422,384 A | 6/1995 | Samuels et al. | 6,334,182 B2 | 12/2001 | Merchant et al. |
| 5,425,951 A | 6/1995 | Goodrich, Jr. et al. | 6,358,530 B1 | 3/2002 | Eljamal et al. |
| 5,447,151 A | 9/1995 | Bruna et al. | 6,365,190 B1 | 4/2002 | Gordon et al. |
| 5,453,514 A | 9/1995 | Niigata et al. | 6,372,258 B1 | 4/2002 | Platz et al. |
| 5,458,135 A | 10/1995 | Patton | 6,402,733 B1 | 6/2002 | Daugherty |
| 5,482,927 A | 1/1996 | Maniar et al. | 6,423,334 B1 | 7/2002 | Brayden et al. |
| 5,506,203 A * | 4/1996 | Backstrom et al. ............. 514/4 | 6,423,344 B1 | 7/2002 | Platz et al. |
| 5,512,547 A | 4/1996 | Johnson et al. | 6,426,210 B1 | 7/2002 | Franks et al. |
| 5,518,709 A | 5/1996 | Sutton et al. | 6,468,782 B1 | 10/2002 | Tunnacliffe et al. |
| 5,518,998 A | 5/1996 | Backstrom et al. | 6,479,049 B1 | 11/2002 | Platz et al. |
| 5,547,696 A | 8/1996 | S.o slashed.rensen | 6,503,411 B1 | 1/2003 | Franks et al. |
| 5,558,085 A | 9/1996 | Rubsamen et al. | 6,509,006 B1 | 1/2003 | Platz et al. |
| 5,567,439 A | 10/1996 | Myers et al. | 6,514,496 B1 | 2/2003 | Platz et al. |
| 5,571,499 A | 11/1996 | Hafler et al. | 6,518,239 B1 | 2/2003 | Kuo et al. |
| 5,580,859 A | 12/1996 | Felgner et al. | 6,565,841 B1 | 5/2003 | Niven et al. |
| 5,589,167 A | 12/1996 | Cleland et al. | 6,565,871 B2 | 5/2003 | Kampinga et al. |
| 5,591,453 A | 1/1997 | Ducheyne et al. | 6,569,406 B2 | 5/2003 | Stevenson et al. |
| 5,607,915 A | 3/1997 | Patton | 6,569,458 B1 | 5/2003 | Gombotz et al. |
| 5,611,344 A | 3/1997 | Bernstein et al. | 6,572,893 B2 | 6/2003 | Gordon et al. |
| 5,618,786 A | 4/1997 | Roosdorp et al. | 6,582,728 B1 | 6/2003 | Platz et al. |
| 5,619,984 A | 4/1997 | Hodson et al. | 6,586,006 B2 | 7/2003 | Duffy et al. |
| 5,621,094 A | 4/1997 | Roser et al. | 6,589,560 B2 | 7/2003 | Foster et al. |
| 5,631,225 A | 5/1997 | Sorensen | 6,592,904 B2 | 7/2003 | Platz et al. |

| | | | | | | |
|---|---|---|---|---|---|---|
| 6,630,169 | B1 | 10/2003 | Bot et al. | EP | 0415567 | 3/1991 |
| 6,649,911 | B2 | 11/2003 | Kawato | EP | 0430045 | 6/1991 |
| 6,655,379 | B2 | 12/2003 | Clark et al. | EP | 0433679 | 6/1991 |
| 6,673,335 | B1 | 1/2004 | Platz et al. | EP | 0 467 172 | 1/1992 |
| 6,681,767 | B1 | 1/2004 | Patton et al. | EP | 0 468 914 | 1/1992 |
| 6,685,967 | B1 | 2/2004 | Patton et al. | EP | 0463653 | 1/1992 |
| 6,737,045 | B2 | 5/2004 | Patton et al. | EP | 0474874 | 3/1992 |
| 6,737,066 | B1 | 5/2004 | Moss | EP | 0 490 797 | 6/1992 |
| 6,752,893 | B2 | 6/2004 | Frieder, Jr. | EP | 0 506 293 | 9/1992 |
| 6,797,258 | B2 | 9/2004 | Platz et al. | EP | 0 520 748 | 12/1992 |
| 6,811,792 | B2 | 11/2004 | Roser et al. | EP | 0 582 459 | 2/1994 |
| 6,825,031 | B2 | 11/2004 | Franks et al. | EP | 0600730 | 6/1994 |
| 6,893,657 | B2 | 5/2005 | Roser et al. | EP | 0 606 486 | 7/1994 |
| 6,921,527 | B2 | 7/2005 | Platz et al. | EP | 0 611 567 | 8/1994 |
| 2002/0127188 | A1 | 9/2002 | Platz et al. | EP | 0616524 | 9/1994 |
| 2002/0132787 | A1 | 9/2002 | Eljamal et al. | EP | 0 655 237 | 5/1995 |
| 2002/0192164 | A1 | 12/2002 | Patton et al. | EP | 0714905 | 6/1996 |
| 2003/0035778 | A1 | 2/2003 | Platz et al. | ES | 8403520 | 2/1983 |
| 2003/0068279 | A1 | 4/2003 | Platz et al. | FR | 2257351 | 1/1974 |
| 2003/0072718 | A1 | 4/2003 | Platz et al. | FR | 2238476 | 2/1975 |
| 2003/0086877 | A1 | 5/2003 | Platz et al. | GB | 0821036 | 9/1959 |
| 2003/0092666 | A1 | 5/2003 | Eljamal et al. | GB | 1122284 | 8/1968 |
| 2003/0113273 | A1 | 6/2003 | Patton et al. | GB | 1182779 | 3/1970 |
| 2003/0113900 | A1 | 6/2003 | Tunnacliffe et al. | GB | 1 288 094 | 9/1972 |
| 2003/0171282 | A1 | 9/2003 | Patton | GB | 1381588 | 1/1975 |
| 2003/0185765 | A1 | 10/2003 | Platz et al. | GB | 1 477 775 | 6/1977 |
| 2003/0198601 | A1 | 10/2003 | Platz et al. | GB | 1 527 605 | 10/1978 |
| 2003/0203036 | A1 | 10/2003 | Gordon et al. | GB | 1533012 | 11/1978 |
| 2003/0215512 | A1 | 11/2003 | Foster et al. | GB | 2 105 189 | 3/1983 |
| 2003/0215514 | A1 | 11/2003 | Platz et al. | GB | 2 126 588 | 3/1984 |
| 2004/0052825 | A1 | 3/2004 | Roser et al. | GB | 2187191 | 9/1987 |
| 2004/0096400 | A1 | 5/2004 | Patton et al. | JP | 52-139789 | 11/1977 |
| 2004/0096401 | A1 | 5/2004 | Patton et al. | JP | 56 138110 | * 10/1981 |
| 2004/0219206 | A1 | 11/2004 | Roser et al. | JP | 56138110 | 10/1981 |
| 2005/0147566 | A1 | 7/2005 | Fleming et al. | JP | 56138111 | 10/1981 |
| 2005/0186143 | A1 | 8/2005 | Stevenson et al. | JP | 59095885 | 2/1984 |
| 2005/0203002 | A1 | 9/2005 | Tzannis et al. | JP | 60-244288 | 12/1985 |
| | | | | JP | 61293201 | 12/1986 |
| | | FOREIGN PATENT DOCUMENTS | | JP | 62-228272 | 10/1987 |
| | | | | JP | 62-255434 | 11/1987 |
| DE | | 1080265 | 4/1960 | JP | 62267238 | 11/1987 |
| DE | | 18 12 574 | 6/1970 | JP | 02084401 | 3/1990 |
| DE | | 24 15 159 | 10/1975 | JP | 03264537 | 11/1991 |
| DE | | 31 41 498 | 4/1983 | JP | 06-100464 | 4/1994 |
| DE | | 01 61 072 | 9/1984 | NL | 7712041 | 5/1979 |
| DE | | 3713326 | 10/1987 | RU | 0628930 | 9/1978 |
| EP | | 0 015 123 | 9/1980 | RU | 0883174 | 11/1981 |
| EP | | 0 072 046 | 2/1983 | RU | 1003926 | 3/1983 |
| EP | | 0090356 | 10/1983 | WO | 84/00294 | 2/1984 |
| EP | | 0 111 216 | 6/1984 | WO | 86/04095 | 7/1986 |
| EP | | 0 122 036 | 10/1984 | WO | 87/00196 | 1/1987 |
| EP | | 0136030 | 4/1985 | WO | 87/02038 | 4/1987 |
| EP | | 0 140 489 | 5/1985 | WO | 87/05300 | 9/1987 |
| EP | | 0139286 | 5/1985 | WO | 88/04556 | 6/1988 |
| EP | | 0 193 372 | 9/1986 | WO | 88/08298 | 11/1988 |
| EP | | 0222313 | 5/1987 | WO | 88/09163 | 12/1988 |
| EP | | 0 229 810 | 7/1987 | WO | 89/06976 | 8/1989 |
| EP | | 0 237 507 | 9/1987 | WO | 89/09614 | 10/1989 |
| EP | | 0251631 | 1/1988 | WO | 90/04962 | 5/1990 |
| EP | | 0 257 915 | 3/1988 | WO | 90/05182 | 5/1990 |
| EP | | 0257956 | 3/1988 | WO | 90/07351 | 7/1990 |
| EP | | 0282179 | 9/1988 | WO | 90/09780 | 9/1990 |
| EP | | 0 289 336 | 11/1988 | WO | 90/11756 | 10/1990 |
| EP | | 0 302 772 | 2/1989 | WO | 90/13285 | 11/1990 |
| EP | | 0315875 | 5/1989 | WO | 90/13328 | 11/1990 |
| EP | | 0325936 | 8/1989 | WO | 90/15635 | 12/1990 |
| EP | | 0 347 779 | 12/1989 | WO | 91/02545 | 3/1991 |
| EP | | 0356154 | 2/1990 | WO | 91/02558 | 3/1991 |
| EP | | 0 360 340 | * 3/1990 | WO | 91/06282 | 5/1991 |
| EP | | 0 364 235 | 4/1990 | WO | 91/11179 | 8/1991 |
| EP | | 0 366 303 | 5/1990 | WO | 91/16038 | 10/1991 |
| EP | | 0 383 569 | 8/1990 | WO | 91/16882 | 11/1991 |
| EP | | 0 407 028 | 1/1991 | WO | 91/18091 | 11/1991 |

| | | |
|---|---|---|
| WO | 92/02133 | 2/1992 |
| WO | 92/10229 | 6/1992 |
| WO | 92/18164 | 10/1992 |
| WO | 92/19243 | 11/1992 |
| WO | 93/00951 * | 1/1993 |
| WO | 93/02712 | 2/1993 |
| WO | 93/02834 | 2/1993 |
| WO | 93/09832 | 5/1993 |
| WO | 93/10758 | 6/1993 |
| WO | 93/11746 | 6/1993 |
| WO | 93/12240 | 6/1993 |
| WO | 93/13752 | 7/1993 |
| WO | 93/17663 | 9/1993 |
| WO | 93/23065 | 11/1993 |
| WO | 93/23110 | 11/1993 |
| WO | 94/00291 | 1/1994 |
| WO | 94/07514 | 4/1994 |
| WO | 94/08552 | 4/1994 |
| WO | 94/13271 | 6/1994 |
| WO | 94/16717 | 8/1994 |
| WO | 94/22423 | 10/1994 |
| WO | 94/24263 | 10/1994 |
| WO | 95/00127 | 1/1995 |
| WO | 95/00128 | 1/1995 |
| WO | 95/01324 | 1/1995 |
| WO | 95/06126 | 3/1995 |
| WO | 95/11666 | 5/1995 |
| WO | 95/20979 | 8/1995 |
| WO | 95/23613 | 9/1995 |
| WO | 95/24183 | 9/1995 |
| WO | 95/31479 | 11/1995 |
| WO | 95/33488 | 12/1995 |
| WO | 96/03978 | 2/1996 |
| WO | 96/09085 | 3/1996 |
| WO | 96/09814 | 4/1996 |
| WO | 96/27393 | 9/1996 |
| WO | 96/32096 | 10/1996 |
| WO | 96/32149 | 10/1996 |
| WO | 96/40049 | 12/1996 |
| WO | 96/40077 | 12/1996 |
| WO | 97/03649 | 2/1997 |
| WO | 97/34689 | 9/1997 |
| WO | 97/41833 | 11/1997 |
| WO | 98/16205 | 4/1998 |
| WO | 98/24882 | 6/1998 |
| WO | 98/58989 | 12/1998 |
| WO | 01/87278 | 11/2001 |
| ZA | 94/00155 | 7/1995 |

OTHER PUBLICATIONS

Annear, "Observations on Drying Bacteria from the Frozen and from the Liquid State," Austral. J. Exp. Biol. (1958), 36:211-221.
Björk et al., "Degradable Starch Microspheres as a Nasal Delivery System for Insulin" International J. of Pharmaceutics (1988), 47:233-238.
Bohnet, "Calculation and Design of Gas/Solid-Injectors," Powder Tech. (1984), pp. 302-313.
Bone et al., "Dielectric Studies of Protein Hydration and Hydration-Induced Flexibility," J. Mol. Biol. (1985), 181:323-326.
Bruni et al., "Glass Transitions in Soybean Seed, Relevance to Anhydrous Biology," Plant Physiol. (1991), 96:660-663.
Budrik et al., "Ejector Feeders for Pneumatic Transport Systems," Chemical & Petroleum Engineering, Sep.-Oct. 1978, 14(9-10):9-10.
Burke, "The Glassy State and Survival of Anhydrous Biological Systems," Membranes, Metabolism and Dry Organisms, Appendix D, 1986, A. Carl Leopold Editor, pp. 358-363.
Byron et al., "Drug Delivery Via the Respiratory Tract," J. of Aerosol Medicine (1994), 7(1):49-75.
Caffrey et al., "Lipid-Sugar Interactions, Relevance to Anhydrous Biology," Plant Physiol. (1988), 86:754-758.
Carpenter et al., "Stabilization of Phosphofructokinase During Air-Drying with Sugars and Sugar/Transition Metal Mixtures," Cryobiology (1987), 24:455-464.
Carpenter et al., "Stabilization of Phosphofructokinase with Sugars During Freeze-Drying: Characterization of Enhanced Protection in the Presence of Divalent Cations," Biochimica et Bipophysica Acta (1987), 923:109-115.
Carpenter et al., "Modes of Stabilization of a Protein by Organic Solutes During Desiccation," Cryobiology (1988), 25:459-470.
Chien et al., "Intranasal Drug Delivery for Systemic Medications," CRC Critical Reviews in Therapeutic Drug Carrier Systems (1987), 4(2):67-92.
Chopin et al., "Destruction de Microbacterium Lacticum, Escherichia coli et Staphylococcus aureus au cours du schage du lait par atomisation," Can. Microbiol. (1977), 23:716-720. No translation.
Colthrope et al., "The Pharmacokinetics of Pulmonary-Derived Insulin: A Comparison of Intratracheal and Aerosol Administration to the Rabbit," Pharm. Res. (1992), 9(6):764-768.
Crowe et al., "Stabilization of Dry Phospholipid Bilayers and Proteins by Sugars," Biochem. J. (1987), 242:1-10.
Crowe et al., "Are Freezing and Dehydration Similar Stress Vectors? A Comparison of Modes of Interaction of Stabilizing Solutes with Biomolecules," Cryobiology (1990), 27:219-231.
Duchateau, "Bile Salts and Intranasal Drug Absorption," International J. of Pharmaceutics (1986), 31:193-199.
Dolovich, "Lung Dose, Distribution, and Clinical Response to Therapeutic Aerosols," Aerosol Sci. and Tech. (1993), 18:230-240.
Elliot et al., "Parental Absorption of Insulin for the Lung in Diabetic Children," Aust. Paediatr. J. (1987), 23:293-297.
Fahy, "The Relevance of Cryoprotectant 'Toxicity' to Cryobiology," Cryobiology (1986), 23:1-13.
Finney et al., "Protein Hydration and Enzyme Activity: The Role of Hydration Induced Conformation and Dynamic Changes in the Activity of Lysozyme," Comments Mol. Cell. Biophys. (1984), 2(3-4):129-151.
Flink, Chapter 17 entitled "Structure and Structure Transitions in Dried Carbohydrate Materials," Physical Properties of Foods, 1983, M. Peleg and E. B. Bagley (Editions), pp. 473-521.
Fox et al., "Performance of a Venturi Eductor as a Feeder in a Pneumatic Conveying System," Powder & Bulk Engineering, Mar. 1988, pp. 33-36.
Friedmann, "Progress Toward Human Gene Therapy," Science Jun. 16, 1989, 244:1275-1281.
Gänsslen, "Uber Inhalation Von Insulin" Klin. Wochenschr. Jan. 1925, 4:71, (with translation).
Gendler et al., "Permethyk Analogue of the Pyrrolic Antibiotic Disctamycin A," J. Med. Chem. (1981), 24(1):33-38.
Goetz, Editor, Chapter Climate and Weather entitled "Atmospheric Humidity and Precipitation," The New Encyclopedia Britannica (1985), 16:476-479.
Govinda, Aerosol Insulin Inhalation Enquiry, Indian J. Physiol. Pharmacol. (1959), 3:161-167.
Green et al., "Phase Relations and Vitrification in Saccharide-Water Solutions and The Trehalose Anomaly," J. Phys. Chem. (1989), 93:2880-2882.
Habener, "Parathyroid Hormone: Secretion and Metabolism In Vivo," Proc. Nat. Acad. Sci., USA, Dec. 1971, 68(12):2986-2991.
Hastings et al., Clearance of Different-Sized Proteins from the Alveolar Space in Humans and Rabbits J. Appl. Physiol. (1992), 73:1310-1316.
Heinemann et al., "Time-Action Profile of Inhaled Insulin," Diabetic Medicine (1997), 14:63-72.
Herrington, "Some Physico-Chemical Properties of Lactose: The Spontaneous Crystallization of Super-Saturated Solutions of Lactose," J. Dairy Science (1934), 17:501-518.
Hesch, "Pulsatile Secretion of Parathyroid Hormone and Its Action on a Type I and Type II PTH Receptor: A Hypothesis for Understanding Osteoporosis," Calcified Tissue Int. (1988), 42:341-344.
Hubbard et al., "Strategies for Aerosol Therapy of $\alpha_1$-Antitrypsin Deficiency by the Aerosol Route," Lung, 1990, 168, Supplement 1990, Proceedings of the 8$^{th}$ Congress of SEP, Edited by H. Matthys, pp. 565-578.

Iijima et al., "A Method for Preservation of Bacteria and Bacteriophages by Drying in Vacuo," Cryobiology (1973), 10:379-385.

Josic, "Optimization of Process Conditions for the Production of Active Dry yeast," Lebensm-Wiss. U. Technol. (1982), 15(1):5-14.

Karel, "Water Relation of Foods," R. B. Duckworth, Ed. (1975), Academic Press, NY, pp. 648-649.

Kauzmann, "The Nature of the Glassy State and The Behavior of Liquids at Low Temperatures," Department of Chemistry, Princeton University, Princetown, New Jersey, Received Mar. 1, 1948, pp. 219-227.

Kim et al., "Survival of Lactic Acid Bacteria During Spray Drying of Plain Yogurt," J. of food Sci. (1990), 55(4):1008-1010, 1048.

Köhler, Diabetes JADA, Feb. 1984 (Abstract).

Köhler, "Islet Alteration in Vitro by Human Lymphocytes and Serum Before and After Manifestation of Type 1 (Insulin-Dependent) Diabetes Mellitus," May 1986, Diabetes, 35, Supplement 1, Program 46th Annual Meeting, Minutes of the 21st General Assembly of the European Association for the Study of Diabetes, p. 559A, No. 270 in the Abstract Part.

Köhler et al., "Nicht Radioaktives Verfahren Zur Messung Der Lungenpermeabilität: Inhalation Von Insulin," Atemu. Lugenkrkh. Jahrgang (1987), 13(6):230-232. For English Abstract see Schlüter Reference.

Köhler, "Aerosols for Systemic Treatment," Lung (1990), pp. 667-684.

Köhler, Chapter 12 entitled "Systemic Therapy with Aerosols," Aerosols in Medicine, Principles, Diagnosis and Therapy, 2nd ed. (1993), published by Elsevier, pp. 303-319.

Labuza et al., Engineering Factors in Single-Cell Protein Production Biotechnology and Bioengineering (1970), 12:135-140.

Laube et al., "Preliminary Study of the Efficacy of Insulin Aerosol Delivered by Oral Inhalation in Diabetic Patients" JAMA (1993), 269(16):2106-2109.

Lee et al., "Development of an Aerosol Dosage Form Containing Insulin" J. of Pharmaceutical Sci. (1976), 65(4):567-572.

Levine et al., "A Polymer Physico-Chemical Approach to the Study of Commercial Starch Hydrolysis Products (SHPs)," Carbohydrate Polymers (1986), 6:213-244.

Levine et al., "Principles of 'Cryostabilization' Technology From Structure/Property Relationships of Carbohydrate/Water Systems," Cryo-letters (1988), 9:21-63.

Liu E al., "Pulmonary Delivery of Free and Liposomal Insulin" Pharmaceutical Research (1993), 10(2):228-232.

Malik, "A Simplified Liquid-Drying Method for the Preservation of Microorganisms Sensitive to Freezing and Freeze-Drying," J. of Microbiological Methods (1990), 12:125-132.

Metwally et al., "Spray Drying of Lactic Acid Culture, I. The Effect of Spray Drying Conditions on the Survival of Microorganisms," Egyptian J. Dairy Sci. (1989), 17:35-43.

Metwally et al., Spray Drying of Lactic Acid Cultures, II. The Effect of Culture Conditions and Storage in Microorganisms, Egyptian J. Dairy Sci. (1989), 17:273-275, 278.

Mumenthaler et al., "Feasibility Study on Spray-Drying Protein Pharmaceuticals: Recombinant Human Growth Hormone and Tissue-Type Plasminogen Activator," Pharmaceutical Research (1994), 11(1): 12-20, Plenum Publishing Corporation.

Nagai et al., "Powder Dosage Form of Insulin for Nasal Administration" J. of Controlled Release (1984), 1:15-22.

Nagano et al., "New Method of Insulin Therapy: Transpulmonary Absorption of Insulin" Jikeikal Med. (1985), 32(3):503-506.

Neer et al., The Use of Parathyroid Hormone Plus 1, 25-Dihydroxyvitamin D to Increase Trabecular Bone in Osteoporotic Men and Postmenopausal Women, Osteoporosis (1987), 53:829-835.

Nieminen et al., Aerosol Deposition in Automatic Dosimeter Nebulization, Eur. J. Respir. Dis. (1987), 71:145-152.

Patton et al., "(D) Routes of Delivery: Case Studies—(2) Pulmonary Delivery of Peptides and Proteins for Systemic Action," Advanced Drug Delivery Reviews (1992), 8:179-196.

Peri et al., "Thermodynamics of Water Sorption on Sacc. Cerevisiae and Cell Viability During Spray-Drying," Lebensm—Wiss. U. Technol. (1974), 7(2)76-81.

Pikal et al., "Moisture Transfer From Stopper to Product and Resulting Stability Implications," Developments in Biological Standardization (1991), 74:165-179, International Symposium on Biological Product Freeze-Drying and Formulation.

Pikal, "Polymorphisms in Pharmaceutical Solids," AAPS, Nov. 15-19, 1992, Annual Meeting and Expositions, San Antonio, TX, 2 pages.

Pittman et al., "Pneumatic Conveying of Bulk Solids Using a Vacuum Aerated Feed Nozzle," Solid Handling Conference Paper C4, Jun. 10-12, 1986, Thames Polytechnic London, United Kingdom, pp. C41-C51.

Poole et al., "Hydration-Induced Conformational and Flexibility Changes in Lysozyme at Low Water Contents," Int. J. Biol. Macromol., Oct. 1983, 5:308-310.

Poole et al., "Sequential Hydration of a Dry Globular Protein," Biopolymers (1983), 22:255-260.

Prajapati et al., "Survival of Lactobacillus acidophilus in Blended—Spray Dried Acidophilus Preparations," Australian J. of Dairy Technology, Mar./Jun. 1987, pp. 17-21.

Rao, "Aerosol Insulin Inhalation Enquiry," Indian J. Physiol. Pharmacol. (1959), 3:161-167.

Roos et al., "Effects of Glass Transitions on Dynamic Phenomena, Figure 10.8," The Glassy State in Foods, published by J. M. Blanchard and P. J. Lillford (Nillington University Press) 1993, one page.

Rosenfeld et al., "Adenovirus-Mediated Transfer of a Recombinant $\alpha$-1-Antitryspin Gene to the Lung Epithelium in Vivo," Science, Apr. 19, 1991, 252:431-434.

Roser, "Trehalose Drying: A Novel Replacement for Freeze-Drying," Biopharm., Sep. 1991, 4(8):47-53.

Ryden et al., "Effect of Polymers and Microspheres on the Nasal Absorption of Insulin in Rats," International J. of Pharmaceutics (1992), 83:1-10.

Sakr, "A New Approach for Insulin Delivery via the Pulmonary Route: Design and Pharmcokinetics in Non-Diabetic Rabbits" International J. of Pharmaceuticals (1992), 86:1-7.

Schlute et al., Abstract Diabetes (1984), 13(6):230-232.

Schneider et al., "Thermostability of Enzyme in the Three-Dimensional Network of Polisaccharide Chains," Bulletin de 1 Academie Polonaise des Sciences (1968), Cl. II, Vol. XVI, No. 4, 1968, Serie des Sciences Biologiques, pp. 203-204.

Skrabanja et al., "Lyophilization of Biotechnology Products," PDA J. of Pharmaceutical Sci. & Tech., Nov.-Dec. 1994, 48(6):311-317.

Slade et al., "Structural Stability of Intermediate Moisture Food—A New Understanding?" Food Structure, Its Creation and Evaluation (1988), pp. 115-147.

Stribling et al., "The Mouse as a Model for Cationic Liposome-Based, Aerosolized Gene Delivery," J. of Biopharmaceutical Sci. (1992), 3 (1/2), pp. 255-263.

Tertyshny et al., "Effect of Orthophosphoric Acid on Survivability of Proionibacterium Shermanii After Spray Drying and in the Process of Storage," Microbiolgy J. (1988), 50(3):49-52, English Summary on p. 52.

Townsend et al., "Use of Lyoprotectants in the Freeze-Drying of a Model Protein, Ribonuclease A," J. of Parenteral Sci. & Tech., Nov.-Dec. 1988, 42(6):190-199.

Tsourouflis et al., "Loss of Structure in Freeze-Dried Carbohydrates Solutions: Effect of Temperature, Moisture Content and Composition," J. Sci. Fd Agric. (1976), 27:509-519.

Uedaira et al., "The Effect of Sugars on the Thermal Denaturation of Lysozyme," Bulletin of the Chemical Society of Japan, Sep. 1980, 53:2451-2455.

Underwood et al., "A Novel Technique for the Administration of Bronchodilator Drugs Formulated as Dry Powders to the Anaesthetized Guinea Pig," J. of Pharmacological Methods (1991), 26:203-210.

Van De Beek et al., "Preservation of the Enzymatic Activity of Rennin During Spray Drying and During Storage, and the Effect of Sugar and Certain other Activities," Neth. Milk Dairy J. (1969), 23:46-54.

Wettlaufer et al., "Relevance of Amadori and Maillard Product to Seed Deterioration," Plant Physiol. Apr. 1991, 97:165-169.

White et al., "The Glassy State in Certain Sugar-Containing Food Products," J. Food Technol. (1966), 1:73-92.

Wigley et al., "Insulin Across Respiratory Mucosae by Aerosol Delivery," Diabetes (1971), 20(8):552-556.

Williams et al., Vial Breakage by Frozen Mannitol Solutions: Correlation with Terminal Characteristics and Effect of Stereoisomerism, Additives, and Vial Configuration, J. of Parenteral Sci. & Tech., Mar.-Apr. 1991, 45(2):94-100.

Williams et al., "The Glassy State in Corn Embryos," Plant Physiol. (1989), 89:977-981.

Witham, "Dry Dispersion with Sonic Velocity Nozzles," Workshop on Dissemination Techniques for Smoke and Obscurants Chemical Systems Laboratory, Aberdeen Proving Group, MD, Mar. 14-16, 1983, pp. 1-26.

Yoshida et al., "Absorption of Insulin Delivered to Rabbit Trachea Using Aerosol Dosage Form," J. of. Pharmaceutical Sci., May 1979, 68(5):670-671.

Zholob et al., "Effect of Injector Unit Design on the Particle Size of Atomized Powder," 0038-5735/79/1806, 1979 Plenum Publishing Corporation, pp. 362-354, Dnepropetrovsk State University, Translated from Poroshkovaya Metallurgiya, Jun. 1979, No. 6(198), pp. 13-16, original article submitted Aug. 1, 1978.

Abstracts, 18$^{th}$ Annual Meeting, Cryobiology, vol. 18, No. 6, Dec. 1981, see Nos. 20 p. 617 & 24 p. 618. Author Gregory Fahy.

Abstract—Japanese Patents Gazette—Week 8604—Apr. 12, 1985, Section Chemical JP 60244288-A, Applicant: Okura Seiyaku KK, one pages, and translation in English.

Abstract—Japanese Patents Gazette—Week 8746—Jul. 10, 1987, Section Chemical JP 62228272-A, Applicant: Amano Pharm. KK, one page.

Abstract—Japanese Patent Gazette—Week 8750—Section Chemical JP 62255434-A Fuji Seiyu KK—Nov. 7, 1987—Inventors: Tagawa Kunio and Kurosawa Wahei—Applicant: Fuji Oil Co. Ltd.

"Clean-Up with Pulsed Jets," Manufacturing Chemist, Apr. 1992, pp. 29, 31.

Drytec, Compact Laboratory Dryer, Undated Brochure, one page.

Lab-Plant Ltd., SD-04 Laboratory Scale Spray Drier, Undated Brochure, 4 pages.

Pharmacia LKB Biotechnology Brochure entitled "A Cure for the Common Cold- Ready to go DNA Labeling Kit Pre-Mixed Reactions that Store at Room Temperature," Undated, 9 pages.

"Production of Trehalose Dried Eggs," D5, Tg Measurements, Undated, 10 pages.

Graham et al., "An in-vitro test for the duration of action of insulin suspension", J. of Pharm. Pharmocol., 36(7):427-430, (Jul. 1984), Abstract.

Heubner et al., "Über Inhalation Von Insulin", J. Klia. Wochenschrift, 3(28):2342-2343.

Schulter et al., "Pulmonary Administration of Human Insulin in Volunteers and Type 1-Diabetics," 75A, 298, (1984).

Vidgren et al., "In Vitro and In Vivo Deposition of Drug Particles Inhaled from Pressurized Aerosol and Dry Powder Inhaler", pp. 2649-2665, (1988).

Adjei, et al., "Pulmonary delivery of therapeutic peptides and proteins", J. Controlled Release, 29:361-373, (1994).

Advertisement for "Stop'a Grow" Manufactured by The Mentholatum Co. Ltd., East Kilbride Scotland G74 5P3.

Agrimi, et al., "Amyloid, Amyloid-Inducers, Cytokines and Heavy Metals in Scrapie and Other Human and Animal Subacute Spongiform Encephalopathies: Some Hypotheses", Med. Hypotheses, 40(2):113-116, (1993).

Ahlneck, et al., "The Molecular Basis of Moisture Effects on the physical and Chemical Stability of Drugs in the Solid State", State Int. J. Pharm., 62:87-95, (1990).

Akers, et al., "Clycine Crystallization During Freezing: The Effects of Salt Form, pH, and Ionic Strength", Pharmaceutical Research, 12(10):1457-1461, (1995).

Akoh, et al., "One-state synthesis of raffinose fatty acid polyesters", J. Food Sci., 52(6):1570-1576, (1987).

Alberts, et al., Molecular Biology of the Cell, 2nd ed., Garland Publishing, Inc., Ch. 2, p. 58, (1989).

Aldous, et al., "The Crystallization of Hydrates from Amorphous Carbohydrates", Cryo-Letters, 16:181-186, (1995).

Aldrich, et al., "Use of the spinning disk technique to produce monodisperse microspheres of human serum albumin for labeling with readioisotopes", J. Applied Radiation and Isotopes, 25:15-18, (1974).

Allen, et al., "Determination of the Degree of Crystallinity in Solid-Solid Equilibria", J. Pharm. Sci., 58(10):1190-1193, (1969).

Allison, et al., "Mechanisms of Protection of Cationic Lipid-DNA Complexes During Lyophilization", Journal of Pharmaceitical Sciences, 89(5):682-691, (2000).

Allison, et al., Lyophilization of Nonviral Gene Delivery Systems, Methods in Molecular Medicine, Nonviral Vectors for Gene Therapy, Ch. 18, 225-251 (Mark A. Findeis ed., Humana Press, 2001).

Anchordoquy, et al., Physical Stabilization of DNA Based Therapeutics, 6(9), DDT 463-470, (May 2001).

Anekwe, et al., "Relaxation Constants as a Predictor of Protein Stabilization," Biocalorimetry: Application of Calorimetry in the Biological Science, J. E. Ladbury and B. Z. Chowdhry, editors, John Wiley & Sons, pp. 243-251, (1998).

Arakawa, et al., "Protein-solvent interactions in pharmaceutical formulations", Pharm. Res., 8(3):285-291, (1991).

Bandara, et al., "Intraarticular Expression of Biologically Active Interleukin IL-Receptor-Antagonist Protein by Ex Vivo Gene Transfer", 90:10764-10768, (Nov. 1993).

Barnett, "Exhubera Inhaled Insulin: A Review", Int. J. Clin. Pract., 58(4):394-401, (2004).

Belopol'Skaya, et al., The Effect of Water as Natural Plasticizer on Thermal Properties of Denatured DNA Studies by Calorimetry 4 Vestnik Sankt-Petersburgskogo Universiteta Seriya pp. 16-22, abstract only, 2 pgs. (1999).

Bell, et al., "Dry Powder Aerosols I: A New Powder Inhalation Device", J. Pharm. Sci., 60(10):1559-1564, (Oct. 1971).

Bigsbee, et al., "Solid State Liability of Insulin: Comparison of Crystalline and Amorphous Forms," Pharmaceutical Research 10(10): Abstract No. PDD 7418, p. S-279, (1993).

Blakely, et al., "Dry instant blood typing plate for bedside use," Lancet, 335:854-855, (1990).

Bögelein, et al., "Influence of Amorphous Mannitol on Powder Properties of Spray Dried Trehalose/Dextran Mixtures", [on-line][retrieved Sep. 2005] Retrieved from the Internet <URL: http://www.pharmtech,unierlangen.de/APV 03 abs/bogelein.pdf> 2 pages (2003).

Bootsma, et al., "β-Cyclodextrin as an Excipient in Solid Oral Dosage Forms: In Vitro and In Vivo Evaluation of Spray-Dried Diazepan-β-Cyclodextrin Products," International Journal of Pharmaceutics, 51:216-223, (1989).

Bosquillon, et al., "Aerosolization Properties, Surface Composition and Physical State of Spray-Dried Protein Powders", Journal of Controlled Release, 99:357-367, (2004).

Branca, et al., "Destructuring effect of trehalose on the tetrahedral network of water: a Rama nand neutron diffraction comparison", Physica A, 304:314-318, (2002).

Branchu, et al. "The Effect of Cyclodextrins on Monomeric Protein Unfolding", Biocalorimetry: Applications of Calorimetry in the Biological Science, J. E. Ladbury and B.Z. Chowdhry (eds.), John Wiley & Sons, Ltd., pp. 297-301, (1998).

Branchu, et al., "Hydroxypropyl-β-Cyclodextrin Inhibits Spray-Drying-Induced Inactivation of (β-Galactosidase", Journal of Pharmaceutical Sciences, 88(9):905-911, (1999).

Brange, et al., "Chemical Stability of Insulin. I. Hydrolytic Degradation During Storage of Pharmaceutical Preparations," Pharmaceutical Research, 9(6):715-726, (1992).

Breitenbach, "Melt Extrusion: From Process to Drug Delivery Technology", European Journal of Pharmaceutics and Biopharmaceutics, 54:107-117, (2002).

Broadhead, et al., "The Spray Drying of Pharmaceuticals", Drug Development and Industrial Pharmacy, 18(11 & 12):1169-1206, (1992).

Broadhead, et al., "The Effect of process and Formulation Variables on the properties of Spray-dried β-Galactosidase", J. Pharm. Pharmacol., 46:458-467, (1994).

Brown, "A Therapeutic Panorama of the Spongiform Encephalopathies", Antiviral Chem. Chemother., 1(2):75-83, (1990).

Budavari, et al., The Merck Index, ONR-57, 12th Edition (1996).

Buitink, et al., High Critical Temperature above Tg May Contribute to the Stability of Biological Systems: Biophysical Journal 79, pp. 1119-1128, (Aug. 2000).

Burvall, et al., "Storage of Lactose-Hydrolised Dried Milk: Effect of Water Activity on the Protein Nutritional Value", Journal of Dairy Research, 45:381-389, (1978).

Byron, et al., Drug Carrier Selection—Important Physicochemical Characteristics Respiratory Drug Delivery, 5th Edition, Interpharm Press, pp. 103-113, (1996).

Bystrom, et al., Microcalorimetry—A Novel Technique for characterization of Powders, Respiratory Drug Delivery IV, Programs and Proceedings, edited by Byron, Dalby and Farr:, pp. 297-302, (1994).

Carpenter, et al., "Rational Design of Stable Lyophilized Protein Formulations: Some Practical Advice", Pharmaceutical Res., 14(8):969-975, (1997).

Casselyn, et al., Time-Resolved Scattering Investigations of Brome Mosaic Virus Microcrystals Appearance D58 Acta Cryst., pp. 1568-1570, (2002).

Caughey, et al., "Sulfhated Polyanion Inhibition of Scrapie-Associated PrP Accumulation in Cultured Cells", J. Virol., 67(2):643-650, (1993).

Chan, et al., "Formulation of Vaccine Adjuvant Muramyldipeptides (MDP). 1. Characterization of Amorphous and Crystalline Forms of a Muramyldipeptide Analogue", Pharmaceutical Research, 5(8):523-527, (1988).

Chan, et al, "Solid State Characterization of Spray-Dried Powders of Recombinant Human Deoxyribonuclease (RhDNase)", Journal of Pharmaceutical Sciences, 87(5):647-654, (1998).

Chan, et al., "Physical Stability of Salmon Calcitonin Spray-Dried Powders for Inhalation" Journal of Pharmaceutical Sciences, 93(3):792-804, (2004).

Chavan, et al., "Effect of Particle Size and Rise in Simulated Inspiratory Flow Rate on Device Emptying in a Dry Powder Inhaler System", [on-line] [retrieved Jan. 7, 2005] Retrieved from the Internet <URL: http://www.aapspharmsci.org/abstracts/AM_1999/1001.htm> 1 page (1999).

Chavan, et al., "Effect of Rise in Simulated Inspiratory Flow Rate and Carrier Particle Size on Powder Emptying From Dry Powder Inhalers", AAPS Pharmsci 2000; 2(2) article 10 [on-line] Retrieved from the Internet <URL: http://www.pharmsci.org> 7 pages (2000).

Chavan, et al., "Novel System to Investigate the Effects of Inhaled Volume and Rates of Rise in Simulated Inspiratory Air Flow on Fine Particle Output From a Dry Powder Inhaler", AAPS Pharmasci 2002; 4(2) article 6 [on-line] Retrieved from the Internet <URL: http://www.aapspharmsci.org> 6 pages (2002).

Chawla, et al., "Production of Spray Dried Salbutamol Sulphate for Use in Dry Powder Aerosol Formulation", International Journal of Pharmaceutics, 108:233-240, (1994).

Chiou, et al., "Pharmaceutical Applications of Solid Dispersion Systems", J. Pharm., 60(9):1281-1302, (1971).

Cleland, et al., "The Development of Stable Protein Formulations: A Close Look at Protein Aggregation, Deamidation and Oxidation", Critical Reviews in Therapeutic Drug Carrier Systems, 10(4):307-377, (1993).

Cline, et al., "Predicting the Quality of Powders for Inhalation From Surface Energy and Area", Pharmaceutical Research, 19(9):1274-1277, (2002).

Cline, et al., "Predicting the Quality of Powders for Inhalation", Respiratory DrugDelivery VIII 683-685, (2002).

Colaco, et al., Extraordinary Stability of Enzymes Dried in Trehalose: Simplified Molecular Biology, Bio/Technology, 10:1007-1011, (1992).

Colaco, et al., "Trehalose Stabilization of Biological Molecules", Biotechnol. Internat., pp 345, 347-350, (1992).

Colaco, et al., "Chapter 14: Chemistry of Protein Stabilization by Trehalose", ACS Symposium Series 567, Formulation and Delivery of Proteins and Peptides, J.L. Cleland & R. Langer, pp. 222-240, (1994).

Considine, et al., Van Nostrand's Scientific Encyclopedia, 9th edition, vol. 2, Wiley-Interscience, John Wiley & Sons, Inc., Definition of Vaccines: pp. 3591-3592, (2002).

Constantino, et al., "Moisture-Induced Aggregation of Lyophilized Insulin", Pharmaceutical Research, 11(1):21-29, (1994).

Constantino, et al., "Effect of Mannitol Crystallization on the Stability and Aerosol Performance of Spray-Dried Pharmaceutical Protein, Recombinant Humanized Anti-IgE Monoclonal Antibody", Journal of Pharmaceutical Sciences, 87(11):1406-1411 (1998).

Craig, et al., "Maillard Reaction Kinetics in Model Preservation Systems in the Vicinity of the Glass Transition: Experiment and Theory", J. Agric. Food Chem., 49(10):4706-4712, (2001).

Crommelin, et al., "Liposomes", Chapter 3, Colloidal Drug Delivery Systems, J. Kreuter, editor: pp. 73-190, (1994).

Crowe, et al. "Is Trehalose Special for Preserving Dry Biomaterials?" Biophysical Journal, 71:2087-2093, (1996).

Crowe, et al., "Interactions of Sugars with Membranes", Biochimica et Biophysica Acta, 947:367-384, (1988).

Crowe, et al., "The Role of Virtification In Anhydrobiosis," Annu. Rev. Physiol., 60:73-103, (1998).

D'Cruz, "Relationship Between Protein Thermal Stability and Glass Transition in Gelatin Polyol and Gelatin-Water Mixtures", Proceedings of 2004 Meeting IFT, Jul. 12-16, 2004, Las Vegas, NV, Session 17E, Food Chemistry: Proteins, [on-line] [retrieved Apr. 6, 2006] Retrieved from the Internet <URL: http://ift.confex.com/ift/2004/techprogram/paper_23006.htm > 17E-4 (2004).

D'Hondt, "Possible Approaches to Develop Vaccines Against Hepatitis A", Vaccine, 10(Suppl. 1):S48-S52m, (1992).

Daemen, et al., "The Destruction of Enzymes and Bacteria During the Spray-Drying of Milk and Whey, 2. The Effect of the Drying Conditions", Neth. Milk Dairy J., 36:211-229, (1982).

Dalby, et al., "Relationship Between Particle Morphology and Drug Release Properties After Hydration of Aerosols Containing Liposome Forming Ingredients", Pharmaceutical Research, 5(10):S-94, Abstract PD 888, (1988).

Dalby, et al., "Droplet Drying and Electrostatic Collection: A Novel Alternative to Conventional Comminution Techniques", J. Biopharm. Sci., 3(1/2):91-99, (1992).

Dalby, et al., "Inhalation Therapy: Technological Milestones in Asthma Treatment", Advanced Drug Delivery, 55:779-791, (2003).

Darrington, et al., "Evidence for a Common Intermediate in Insulin Deamidation and Covalent Dimer Formation: Effects of pH and Aniline Trapping in Dilute Acidic Solutions", Journal of Pharmaceutical Sciences, 84(3):275-282, (1995).

De Carlo, et al., "Unexpected Property of Trehalose as Observed by Cryo-Electron Microscopy", Journal of Microscopy, 196(1):40-45, (1999).

Derwent English abstract for DE 3713326, published Oct. 29, 1987, entitled "Spray dried water-dispersible granulated—prepd. from aq. concentrates contg. Active ingredient and ammonium carbonate or ammonium nitrate".

Derwent English abstract for EP 315875, published May 17, 1989, entitled "Microcapsule prodn. contg. soluble protein or peptide—using mixt. Of polyhdroxy-butyric acid and polyactide-colycolide".

Dose, et al., Survival in Extreme Dryness and DNA-Single-Strand Breaks, Advances in Space Research, 12(4): (4)221-(4)229, (1992).

"Drug Absorption and Availability", Modern Pharmaceutics, 3rd edition, G.S. Banker et ak, (eds), Marcel Dekker, Inc., p. 145, (1996).

During, et al., "Long-Term Behavioral Recovery in Parkinsonian Rats by an HSV Vector Expressing Tyrosine Hydroxylase", Sci. 266(5189):1399-1403, (Nov. 1994), [abstract—1 pg.].

Edwards, et al. "Crystallization of Pure Anhydrous Polymorphs of Carbamazepine by Solution Enhanced Dispersion With Supercritical Fluids (SEDSTM)", Journal of Pharmaceutical Sciences, 90(8):1115-1124, (2001).

Eleutherio, et al., "Role of the Trehalose Carrier in Dehydration Resistance of Saccharomyces Cerevisiae," Biochimica et Biophysica Acta, 1156:263-266, (1993).

Elkordy, et al., "Integrity of Crystalline Lysozyme Exceeds that of a Spray-Dried Form", International Journal of Pharmaceutics, 247:79-90, (2002).

Fahy, et al., "Vitrification as an Approach to Cryopreservation", Cryobiology, 21:407-426, (1984).

Fakes, et al, "Moisture Sorption Vehavior of Selected Bulking Agents Used in Lyophilized Products", PDA J. Pharm Sci. Technol. 54(2): 144-149, Abstract only [on-line] [retrieved Sep. 25, 2005] Retrieved from the Internet < URL: http://www.ncbi.nlm.nih.gov.> (2000).

Finar, "§14. Trehalose, m.p. 203° C.," under "Carbohydrate," Organic Chemistry, vol. 2, Stereochemistry and the Chemistry of Natural Products, 5th edition, Longman, p. 323, (1996).

Forbes, et al., "Water Vapor Sorption Studies on the Physical Stability of a Series of Spray-Dried Protein/Sugar Powders for Inhalation", Journal of Pharmaceutical Sciences, 87(11):1316-1321, (1998).

Franks, "Separation, Improved Freeze-Drying, an Analysis of the Basic Scientific Principles", Process Biochemistry, 24(1): iii-vii, (1989).

Franks, et al., "Freeze Drying: From Empiricism to Predictability", Cyro-Letters, 11:93-110, (1990).

Franks, et al., "Materials Science and the Production to Shelf-Stable Biologicals", Pharm. Tech. Int., 7 pgs., (Oct. 1991).

Franks, "Accelerated Stability Testing of Bioproducts: Attractions and Pitfalls", TIBTECH, 12:114-117, (1994).

French, et al., "Moisture induced state changes in spray-dried trehalose/protein formulations", Pharmaceutical Res., 12(9 Suppl):S83, 8 pages, (1995).

Fukuoka, et al., "Glassy State of Pharmaceuticals. V. Relaxation During Cooling and Heating of Glass by Differential Scanning Calorimetry", Chem. Pharm. Bull., 39(8):2087-2090, (1991).

Graham, et al., "An in-vitro test for the duration of action of insulin suspension", J. Pharm. Pharmacol., 36:427-430, (1984), (PubMed abstract only).

Green, et al., "The Protein-Glass Analogy: Some Insights from Homopeptide Comparisons", J. Phys. Chem., 98:13780-13790, (Apr. 1994).

Gupta, et al., "Single Virus Particle Mass Detection Using Microresonators with Nanoscale Thickness", Applied Physics Letters, 84(11):1976-1978, (2004).

Hahn, et al, "Solid Surfactant Solutions of Active Ingredients in Sugar Esters", Pharmaceutical Research, 6(11):958-960, (1989).

Hancock, et al., "The Use of Solution Theories for Preducting Water Vapor Absorption by Amorphous Pharmeceutical Solids; A Test of the Flory-Huggins and Vrentas Models", Pharmaceutical Research, 10(9):1262-1267, (1993).

Hancock, et al., The Relationship Between the Glass Transition Temperature and the Water Content of Amorphous Pharmaceutical Solids, Pharmaceutical Research, 11(4):471-477, (1994).

Hancock, et al., "Molecular Mobility of Amorphous Pharmaceutical Solids Below Their Glass Transition Temperatures", Pharmaceutical Research, 12(6):799-806, (1995).

Hancock, et al., "Characteristics and Significance of the Amorphous State in Pharmaceutical Systems", J. of Pharmaceutical Sciences, 86(1):1-12, (1997).

Hancock, et al., "A Pragmatic Test of Simple Calorimetric Method for Determining the Fragility of Some Amorphous Pharmaceutical Materials", Pharm Res., 15(5):762-767, (1998).

Hancock, et al., "The Effect of Temperature on Water Vapor Sorption by Some Amorphous Pharmaceutical Sugars", Pharmaceutical Development and Technology, 4(1): 125-131, (1999).

Hanes, et al., "Porous Dry-Powder PLGA Microspheres coated with Lung Surfactant for Systemic Insulin Delivery Via the Lung", Proc. Int;l Symp. Control Rel. Bioactive Matter, 24:57-58, (1997).

Hatley, et al., "Stabilization of Labile Materials by Amorphous Carbohydrates Glass Fragility and the Physiochemical Properties that Make Trehalose a Superior Excipient", Pharmaceutical Research 13(9 Suppl.) PDD, 7165:S274, (1996).

Heitefuss, et al. "The Stabilization of Extracts of Cabbage Leaf Proteins by Polyhydroxy Compounds for Electrophoretic and Immunological Studies," Archives of Biochemistry and Biophysics, 85:200-208, (1959).

Heller, et al., Protein Formulation and Lyophilization Cycle Design: Prevention of Damage Due to Freeze-Concentration Induced Phase Separation 63 Biotechnology & Bioengineering, pp. 166-174, (1999).

Herrington, et al., "Physico-Chemical Studies on Sugar Glasses. I. Rates of Crystallization," Journal of Food Technology, 19:409-425, (1984).

Heubner, et al., "Kurze Wissenschaftliche Mitteilungen", Klin. Wochenschrift, 51:2342-2343, (1924).

Hickey, editor "Methods of Aerosol Particle Size Characterization", Pharmaceutical Inhalation Aerosol Technology, pp. 219-340, (1992).

Hickey, et al., "Behavior of Hygroscopic Pharmaceutical Aerosols and the Influence of Hydrophobic Additives," Pharmaceutical Research, 10(1):1-7, (1993).

Hoener, et al., "Factors Influencing Drug Absorption and Availability", Modern Pharmaceutics, Gilbert S. Banker et al., eds., Marcel Dekker Inc., Chapter 4, pp. 121-153, (1996).

Ibrahim, et al., "Spray Vaccination With an Improved F Newcastle Disease Vaccine. A Comparison of Efficacy With the B1 and La Sota Vaccines," Br. Vet. J., 139:213-219, (1983).

Igaki, et al., "The Inhibition of the Maillard Reaction by L Lysine In-Vitro," J. Jpn. Diabetes Soc., 34(5):403-407, (1991) including English abstract.

Iglesias et al., "Adsorption Isotherm of Amorphoous Trehalose", J. Sci. food Agric., 75:183-186, (1997).

"Immunotherapy of Malignancy by in vivo Gene Transfer into Tumors", Hum. Gene Therapy, 3(4):399-410, (Aug. 1992), [abstract—1 pg.].

IUPAC Compendium of Chemical Terminology, 1$^{st}$ Edition, (1987).

Jameel, et al., "Freeze Drying Properties of Some Oligonucleotides", Pharmaceutical Development and Technology, 6(2):151-157, (2001).

Japanese Patent Publication H3-264537 (English translation), published Nov. 25, 1991, entitled "Method for improving the elution properties of sparingly soluble drugs".

Jovanovic-Peterson, et al., "Jet-injected insulin is associated with decreased antibody production and postprandial glucose variability when compared with needle-injected insulin in gestational diabetic women," Diabetes Care, 16(11):1479-1484, ( Nov. 1993).

Kachura, "Method of Drying Lactic Acid Bacteria," Vinodelie I Vinogradarstvo SSR 2:49-50, English Abtract only, one page (1985).

Kanna, et al. "Denaturation of Fish Muscle Protein by Dehydration" Bull. Tokai Ref. Fish. Res. Lab. 77:70-76, English abstract (1974).

Karmas, et al., "Effect of Glass Transition on Rates of Nonenzymatic Browning in Food Systems", J. Agric. Fodo Chem., 40:873-879, (1992).

Khan, "Chemistry And New Uses Of Sucrose: How Important?" Pure & Appl. Chem., 56(7):833-844, (1984).

Klein, et al., "High Velocity Microprojectiles For Delivering Nucleic Acids Into Living Cells," Nature, 327:70-73, (1987).

Labrude, et al., Protective Effect of Sucrose on Spray Drying of Oxyhemoglobin, J. Pharm. Sci., 78(3):223-229, (Mar. 1989).

Labuza, et al., "Glass Transition Temperatures of Food Systems", [on-line] [retrieved Sep. 2005] Retrieved from the Internet <URL: http://faculty.che.umn.edu/fscn/Ted_Lebuza/PDF_files/ Isotherm_Folder/Tg%20compilation.pdf > pp. 1-31 (Jan. 1992).

Lai, et al., "Solid-state Chemical Stability of Proteins and Peptides", Journal of Pharmaceutical Sciences, 88(5):489-500, (1999).

Laube, et al., Preliminary Study of the Efficacy of Insulin Aerosol Delivered by Oral Inhalation in Diabetic Patients JAMA, 269(16):2106-2109, (1993).

Laube, et al., "Targeting Aerosol Deposition in Patients With Cystic Fibrosis, Effects of Alterations in Particle Size and Inspiratory Flow Rate", Chest 118(4):1069-1076 (2000).

Ledl, et al., "New Aspects of the Maillard Reaction in Foods and in the Human Body," Ang. Chem., Int. Ed. Engl., 29:565-594, (Jun. 1990).

Lee, Developments in Food Carbohydrate—2nd edition Applied Science Publishers, London, Table of Contents, 4 pages, (1980).

Lee, "Spray Drying of Proteins," Chapter 6, Rational Design of Stable Protein Formulations, Theory and Practice, J. F. Carpenter & M. Manning, pp. 135-158, (2002).

Lehninger, Albert L. The Molecular Basis of Cell Structure and Function Biochemistry, Chapter 31, 859-890 (Worth Publishers Inc., 2nd edition, 1975).

Leslie, et al., "Trehalose and sucrose protect both membranes and proteins in intact bacteria during drying", Appl. Env. Microbiol., 61(10):3592-3597, (1995).

Leuner, et al. "Improving Drug Solubility for Oral Delivery Using Solid Dispersions", European Journal of Pharmaceutics and Biopharmaceytics, 50:47-60, (2000).

Levine, et al., "Water as a plasticizer: physico-chemical aspects of low-moisture polymeric systems", in *Water Science Reviews* (Franks, Ed.), vol. 3, Water Dynamics, pp. 79-175, (1988).

Levine, et al., "Another View of Trehalose for Drying and Stabilizing Biological materials", Bio. Pharm., pp. 36-40, (1992).

Li, et al., "Realistic In Vitro Assessment of Dry Powder Inhalers", Respiratory Drug Delivery VIII, pp. 687-689, (2002).

Lin, et al., "Solid Particulates of Drug-β-Cyclodextrin Inclusion Complexes Directly Prepared by a Spray-Drying Technique", International Journal of Pharmaceutics, 56:249-259, (1989).

Liu, et al., "Dynamics of Pharmaceutical Amorphous Solids: The Study of Enthalpy Relaxation by Isothermal Microcalorimetry", Journal of Pharmaceutical Sciences, 91(8):1853-1862, (2002).

Louey, et al., "Controlled Release Products for Respiratory Delivery", APR, 7(4):82-87 [on-line] [retrieved Sep. 2005] Retrieved from the Internet <URL: http://www.americanpharmaceuticalreview.com/article.aspx?article=77>11 pages (2004).

Louis, et al., "Survival Of *Escherichia Coli* During Drying And Storage In The Presence of Compatible Solutes" Appl. Microbiol. Biotechnol., 41:684-688, (1994).

Lueckel, et al., "Effects of Formulation and Process Variables on the Aggregation of Freeze-Dried Interleukin-6 (IL-6) After Lyophilization and on Storage", Pharmaceutical Development and Technology, 3(3):337-346, (1998).

Mackenzie, "Collapse During Freeze Drying-Qualitative and Quantitative Aspects", Freeze Drying and Advanced Food Technology, edited by Goldblith, Rey and Rothmayr, pp. 277-307, (1975).

Makower, et al., "Equilibrium Moisture Content and Crystallizaiton of Amorphous sucrose and Glucose", Ag. and Food Chem., 4(1):72-77, (Jan. 1956).

Martin, et al., "States of Matter and Phase Equilibria", Chapter 4, Physical Pharmacy, Physical Chemical Principles in the Pharmaceutical Sciences, 3rd Edition, pp. 62-92, (1983).

Masters, K., *Spray Drying Handbook*, 5th ed., England; Longman Scientific & Technical and John Wiley & Sons, Inc., pp. 309-352 and pp. 640-642 (1991).

Masters, K., *Spray Drying Handbook*, 5th ed., New York; Longman Scientific & Technical, John Wiley & Sons, Inc., pp. 1-9, 32-33, 67-69, 491-537, 643-662, (1991).

Matsuda, et al., "Amorphism and Physicochemical Stability of Spray Dried Frusemide," J. Pharm. Pharmacol., 44:627-633, received Nov. 7, 1991 (1992).

Mattern, et al., "Formulation of Proteins in Vacuum-Dried Glasses. II. Process and Storage Stability in Sugar-Free Amino Acid Systems", Pharmaceutical Development & Technology, 4(2):199-208, (1999).

Miller, et al., "stabilization of Lactate Dehydrogenase Folliwing Freeze-Thawing and Vacuum-Drying in the Presence of Trehalose and Borate", Pharmaceutical Research, 15(8):1215-1221, (1998).

Molinda, et al., "The Stability of Lyophilized Lipid/DNA Complexes During Prolonged Storage," J. Pharm. Sci. 93(9):2259-2273, abstract only, one page, [on-line] [retrieved Sep. 2004] Retrieved from the Internet <URL: http://www.ncbi.nlm.nih.gov>, (2004).

Monnier, et al., "Mechanisms of Protection Against Damage Mediated by the Maillard Reaction in Aging", Gerontology, 37:152-165, (1991).

Mouradian, et al., "Degradation of Functional Integrity During Long-Term Storage of a Freeze-Dried Biological Membrane", Cryobiology, 22: 119-127, (1985).

Moynihan, et al., "Dependence of the Glass Transition Temperature on Heating and Cooling Rate", J. Physical. Chem., 78(26): 2673-2677, (1974).

Murphy, et al., "Chapter 19: Immunization Against Viruses", Fields of Virology, 2nd Edition, vol. 1, Raven Press, pp. 469-502, (1990).

Murphy, et al., Fields Virology, vol. 1, Chapter 16, Immunization Against Virus Disease, 467, at p. 468, first full paragraph, first column, lines 26-33 (Bernard N. Fields et al. eds., Lippincott-Raven Publishers, 3rd ed. 1996).

Nabel, et al., "Immunotherapy of Malignancy by In Vivo Gene Transfer Into Tumors," Hum. Gene. Ther. 3(4): 399-410 (Aug. 1992) Abstract only [on-line] [retrieved Apr. 7, 2006] Retrieved from the Internet <URL: http://www.ncbi.nlm.nih.gov/entrez/query.fcgi?cmd=Retrieve&db=submed&dopt=Abstr>.

Nabel, et al., "Direct Gene Transfer with DNA-Liposome Complexes in Melanoma: Expression, Biologic Activity, and Lack of Toxicity in Human", Proc. Nat'l. Acad. Sci., USA, 90:11307-11311, (Dec. 1993).

Naini, et al., "Particles for Inhalation Produced by Spray Drying and Electrostatic Precipitation of Different Protein-Sugar Solutions", Respiratory Drug Delivery V, pp. 382-384, (1996).

Naini, et al., "Physicochemical Stability of Crystalline Sugars and Their Spray-Dried Forms: Dependence Upon Relative Humidity and Suitability for Use in Powder Inhalers", Drug Development and Industrial Pharmacy, 24(10):895-909, (1998).

Natarajan, Crystallization Conditions for VIPER Entries [on-line] [retrieved Nov. 4, 2004] Retrieved from the Internet <URL: http://www.xtal.tsinghua.edu.cn/research/groups/web/material/Virus%20Crystallization%2OPage.htm> 5 pages (last updated Jan. 3, 2002).

Newman, et al., "Aerosol Therapy in AIDS", Lung, 168(Suppl.):685-691, (1990).

Niven, "Delivery of Biotherapeutics by Inhalation Aerosols," Pharmaceutical Technology, pp. 72-75, 80, (Jul. 1993).

Niven, "Delivery of Biotherapeutics by Inhalation Aerosol," Critical Reviews in Therapeutic Drug Carrier Systems, 12(2&3):151-231, (1995).

Norberg, et al., "Glass Transition in DNA From Molecular Dynamics Simulation", Proc. Natl. Acad. Sci. USA, 93:10173-10176, (1996).

O'Connor, et al., Remington's Pharmaceutical Sciences, 18th Edition, Chapter 88, "Powders", pp. 1615-1632, (1990).

Odegard, et al., "Inhaled Insulin: Exubera", The Annals of Pharmacotherapy, 39:843-853, (2005).

Ohtake, et al., "Effect of pH, Counter Ion and Phosphate Concentration on the Glass Transition Temperature fo Freeze-Dried Sugar-Phosphate Mixtures", Pharmaceutica Research, 21(9):1615-1621, (2004).

Okamoto, et al., "Dry Powders for Pulmonary Delivery of Peptides and Proteins", Kona, 20:71-83, (2002).

Oksanen, et al., "The Relationship between the Glass Transition Temperature and Water Vapor Absorption by Poly(Vinylpyrrolidone)," Pharmaceutical Research, 7(6): 654-657 and errata on p. 974, (1990).

Okumura, et al., "Intratracheal Delivery of Calcitonin Dry Powder in Rats and Human Volunteers," S.T.P. Pharmaceutical Sciences, 4(1):5 pages, (Jan., Feb. 1994).

Onodera, et al., "Glass Transition of Dehydrated Amorphous Solid", Bull. Chem. Soc. Japan, 41(9):2222, (1968).

Owens, et al., "Alternative Routes of Insulin Delivery," Diabetic Medicine, 20:886-898, (2003).

Palmer, et al. "X-Ray Diffractometer and Microscopic Investigation of Crystallization of Amorphous Sucrose," Agricultural and Food Chemistry, 4(1):77-81, (Jan. 1956).

Parks, "Studies on Glass. II The Transition Between the Glassy and Liquid States in the Case of Glucose", Journal of Physical Chemistry, vol. 31, pp. 1366-1379, (1927).

Patel, et al., "Degradation Kinetics of High Molecular Weight Poly(L Lactide) Microspheres and Release Mechanism of Lipid: DNA Complexes", Journal of Pharmaceutical Sciences, 93(10):2573-2584, (2004).

Patton, "Alternatives to injections: Pulmonary delivery of peptides and proteins", Chapter 16 in *Therapeutic Proteins, Pharmackinetics and Pharmacodynamics*, (King, et al., Eds.), pp. 329-347, (1993).

Pearlman, et al., "Formulation Strategies for Recombinant Proteins: Human Growth Hormone and Tissue Plasminogen Activator", Therapeutic Peptides and Proteins, Formulation, Delivery and Targeting, Cold Spring Harbour, New York, pp. 23-30, (1989).

Pearlman, et al., "Pharmaceutics of Protein Drugs", J. Pharm. Pharmacol., 44(Suppl. 1):178-185, (1992).

Pekarek, et al., "Double-walled polymer microspheres for controlled drug release", Nature, 367:258-260, (1994).

"Pfizer and Inhale Therapeutic Systems Enter Pulmonary Insulin Collaboration for Dry Powder Aerosol Delivery", Health News Daily, 7(13):4-5, (1995).

Phillips, et al., "Size Reduction of Peptides and Proteins by Jet-Milling", Respiratory Drug Delivery VI, pp. 161-167, (1998).

Pikal, et al., "Thermal Decomposition of Amorphous β-Lactam Antibacterials", Journal of Pharmaceutical Science, 66(9):1312-1316, (Sep. 1977).

Pikal, "Freeze-Drying of Proteins Part II: Formulation Selection", Bio. Phar., 3(8):26-30, (Oct. 1990).

Pikal, et al., "The Stability of Insulin in Crystalline and Amorphous Solids: Observation of Greater Stability for the Amorphous Form", Pharmaceutical Research, 14(10):1379-1387, (1997).

Pikal, et al., Errata of "The Stability of Insulin in Crystalline and AmorphousSolids: Observation of Greater Stability for the Amorphous Form," Pharmaceutical Research, 15(2):362-363, (1998).

Pine, et al., "15-3 Oligosaccharides and Polysaccharides," Organic Chemistry, 4th edition, McGraw-Hill International Book Company, p. 763 (1980).

Pisecky, "2. Evaporation and Membrane Filtration", Handbook of Milk Powder Manufacture, Niro A/S, Denmark, p. 3, (1997).

Plautz, et al., "Immunotherapy of malignancy by in vivo gene transfer into tumors", Proc. Natl. acad. Sci. USA, 90:4645-4649, (May 1993), Genetics.

Pocchiari, et al. "Amphotericin B: A Novel Class of Antiscrapie Drugs," J. Infect. Dis., 160(5):795-802, (Nov. 1989).

Prestrelski, et al., "Separation of Freezing- and Drying-Induced Denaturation of Lyophilized Proteins Using Stress-Specific Stabilization," Archives of Biochemistry and Biophysics, 303(2):465-473, (Jun. 1993).

Prestrelski, et al., "Optimization of Lyophilization Conditions for Recombinant Human Interleukin-2 by Dried-State Conformational Analysis Using Fourier-Transform Infrared Spectroscopy," Pharmaceutical Research, 12(9):1250-1259, (1995).

Product Insert for "Humalog® insulin Lispro injection (rDNA Origin)", Eli Lilly and Company, 8 pages (© 1996, 2000).

Quan, Protein Science, 4(Suppl. 2):148, Abstract No. 490-T (1995).

Ramanujam, et al., "Ambient-Temperature-Stable Molecular Biology Reagents," Biotechniques, 14(3):470-473, (1993).

Remington: The Science and Practice of Pharmacy, A. R. Gennaro, 19th edition, Mack Publishing Company, Easton, Pennsylvania 18042, pp. 1517-1518.

Ringe, et al., "The 'Glass Transition in Protein Dynamics: What it is, Why is Occurs, and How to Exploit It", Biophys. Chem. 105(2-3):667-680, Abstraact only, [on-line] [retrieved Nov. 19, 2004] Retrieved from the Internet <URL: http://www.ncbi.nlm.nih.gov> (2003).

Roos, "Phase Transitions of Mixtures of Amorphous Polysaccharides and Sugars", Biotechnology Progress, 7(1):49-53, (1991).

Roos, "Melting and glass transitions of low molecular weight carbohydrates", Carbohydrate Research, 238:39-48, (1993).

Roser, "Trehalose, A New Approach To Premium Dried Foods," Trends in Food Sci. and Tech., pp. 166-169, (Jul. 1991).

Roser, et al. "A Sweeter Way To Fresher Food", New Scientist, pp. 25-28, (May 15, 1993).

Saleki-Gerhardt, et al., "Non-Isothermal and Isothermal Crystallization of Sucrose From the Amorphous State," Pharmaceutical Research, 11(8):1166-1173, (1994).

Saleki-Gerhardt, et al., "Hydration and Dehydration of Crystalline and Amorphous Forms of Raffinose," Journal of Pharmaceutical Sciences, 84(3):318-323, (Mar. 1995).

Sambrook, et al., Molecular Cloning: A Laboratory Manual, 2nd. ed., "Concentrating Nucleic Acids: Precipitation with Ethynol or Isopropanol", pp. E.10-E.17, Cold Spring Harbor Laboratory Press, (1989).

Sanchez, et al., "Recombinant System for Overexpression of Cholera Toxin B Subunit In Vibrio Cholerae as a Basis for Vaccin Development" Proc. Natl. Acad. Sci. USA, 86:481-485, (1989).

Sarkar, et al., "Immunization of Mice Against Murine Mammary Tumor Virus Injection and Mammary Tumor Development", Cancer Research, 38:1468-1472 (1978).

Shamblin, et al., "Enthalpy Relaxation in Binary Amorphous Mixtures Containing Sucrose", Pharmaceutical Research, 15(12):1828-1834, (Dec. 1998).

Schebor, et al., "Color Formation Due to Non-Enzymatic Browning in Amorphous, Glassy, Anhydrous, Model Systems", Food Chemistry, 65:427-432, (1999).

Sciarra, et al., "Aerosols", Remington's Pharmaceutical Sciences, Chap. 93, 17th Ed., Mack Publishing Company, Alfonso R. Gennaro, editor, pp. 1662-1677, (1985).

Sebhatu, et al., "Assessment of the Degree of Disorder in Crystalline Solids by Isothermal Microcalorimetry," International Journal of Pharmaceutics, 104:135-144, (1994).

Sellers, et al., "Dry Powders of Stable Protein Formulations From Aqueous Solutions Prepared Using Supercritical C02-Assisted Aerosolization", Journal of Pharmaceutical Sciences, 90(6):785-797, (2001).

Serajuddin, et al., "Effect of Thermal History on the Glassy State of Indapamide," J. Pharm. Pharmacol., 38:219-220, (1986).

Shalaev, et al., "Structural Glass Transitions and Thermophysical Processes in Amorphous Carbohydrates and Their Supersaturated Solutions", J. Chem. Soc. Farady Trans., 91(10):1511-1517, (1995).

Shalaev, et al., "How Does Residual Water Affect The Solid-State Degradation of Drugs in the Amorphous State", Journal of Pharmaceutical Sciences, 85(11):1137-1141, (1996).

Sharma, et al., "Effect of Vaccum Drying on Protein-Mannitol Interactions: The Physical State of Mannitol and Protein Structure in the Dried State," AAPS PharmSciTech 5(1) Article 10:1-12 [on-line] [retrieved ] Retrieved from the Internet <URL: http://www.aapspharmscitech.org> (2004).

Singer, et al "Thermotolerance in Saccharomyces Cerevisiae: the Yin and Yang of Trehalose", Tibtech, 16:460-468, (1998).

Slade, et al., "Non-Equilibrium Behavior of Small Carbohydrate-Water Systems", Pure and Applied Chemistry, 60(12):1841-1864, (1988).

Slade, et al., The Glassy State Phenomenon in Food Molecules, The Glassy State in Foods, Blanshard & Lillford, editors, pp. 35-101, (1993).

Sokolov, et al., "Glassy Dynamics in DNA: Ruled by Water of Hydration" Journa of Chemical Physics, 110(14):7053-7057, (1999).

Sonner, et al., "Spray-Freeze-Drying for Protein Powder Preparation: Particle Characterization and a Case Study With Trypsinogen Stability", Journal of Pharmaceutical Sciences, 91(10):2122-2139, (2002).

Spi PolyolsTM "What are Polyols? What do Polyols do? What are Polyols' functionality?", [on-line] [retrieved Apr. 6, 2006] Retrieved from the Internet <URL: http://spipolyols.com/whatarepolyols.html> one page (2003).

Stribling, et al., "Aerosol Gene Delivery in vivo", Proc. Nat'l. Acad. Sci., 89:11277-11281, (Dec. 1992).

Strickley, et al., "Solid-State Stability of Human Insulin II. Effect of Water on Reactive Intermediate Partitioning in Lyophiles from pH 2-5 Solutions: Stabilization Against Covalent Dimer Formation", Journal of Pharmaceutical Sciences, 86(6):645-653, (1997).

Strom, et al., "Trehalose Metabolism in *Escherichia coli*: Stress Protection and Stress Regulation of Gene Expression", Molecular Microbiology, 8(2):205-210, (1993).

Stubberud, et al., "The Use of Gravimetry For The Study of the Effect of Additives on the Moisture-Induced Recrystallisation of Amorphous Lactose", International Journal of Pharmaceutics, 163:145-156, (1998).

Sukenik, et al., "Enhancement of a Chemical Reaction Rate by Proper Orientation of Reacting Molecules in the Solid State", J. Am. Chem. Soc., 97(18):5290-5291, (Sep. 1975).

Sussich, et al., "Reversible Dehydration of Trehalose and Anhydrobiosis: From Solution State to an Exotic Crystal?", Carbohydrate Research, 334:165-176, (2001).

Takahashi, et al., "Induction of CD8+ cytotoxic T cells by immunization with purified HIV-1 envelope protein in ISCOMs", Nature 344:873-875, (Apr. 1990).

Tarelli, et al., "Additives to Biological Substances. III. The Moisture Content and Moisture Uptake of Commonly Used Carrier Agents Undergoing Processing Conditions Similar to Those Used in the Preparation of International Biological Standards," Journal of Biological Standardization, 15:331-340, (1987).

Thatcher, "Quantitation of Virus" [on-line] [retrieved Nov. 4, 2004] Retrieved from the Internet <URL: http://www.sonoma.edu/users/t/thatcher/bio1383/lab.htm> 4 pages, (last updated Jan. 5, 2002).

Timko, et al. "Thermal Analysis Studies of Glass Dispersion Systems", Drug Devel. Ind. Phar., 10(3):425-451, (1984).

Timsina, et al., "Drug Delivery to the Respiratory Tract Using Dry Powder Inhalers," International Journal of Pharmaceutics, 101:1-13, (1994).

To, et al., "Collapse, a Structural Transition in Freeze Dried Carbohydrates", J. Fd. Technol., 13:567-581, (1978).

Toyama, (ed) Handbook of Natural Product for food processing, 9th Edition, Osaka, Japan, Shokuhin to Kagaku Sha, pp. 384 and 495 (ISBN4-87994-048-8), (1986).

Uritani, et al., "Protective Effect of Disaccharides on Restriction Endonucleases During Drying Under Vacuum," J. Biochem., 117:774-779, (1995).

Ulrich, "Biophysical Aspects of Using Liposomes as Delivery Vehicles", Bioscience Reports, 22(2):129-150, (2002).

Vain, et al., "Development of the particle inflow gun", Plant Cell, Tissue and Organ Culture, 33:237-246, (1993).

Vavelyuk, et al., "Thermostability of DNA and Its Association with Vitrification", Tsitologiya, 41(11):958-965,.(1999).

Vidgren, et al., "In vitro and in vivo deposition of drug paricles inhaled from pressurized aerosol and dry powder inhaler", Drug Devel. Indust. Pharm., 14:2649-2665, (1983).

Vidgrén, et al., "Comparison of Physical and Inhalation Properties of Spray-Dried and Mechanically Micronized Disodium Cromoglycate," International Journal of Pharmaceutics, 35:139-144, (1987).

Vromans, et al., "Studies on Tableting Properties of Lactose. VII. The Effect of Variations in Primary Particle Size and Percentage of Amorphous Lactose in Spray Dried Lactose Products," International Journal of Pharmaceutics, 35:29-36, (1987).

Wang, et al., eds. Stability and characterization of protein and peptide drugs, Table of Contents, 6 pages, (1993).

Welsh, "The Role of Compatible Solutes In the Adaptation and Survival of *Escherichia Coli*," Ph.D. Thesis Submitted to Department of Biological Sciences, University of Dundee., pp. 1-262, (Aug. 1992).

Whittier, "Lactose and its Utilization: A review", J. Dairy Science, 27:505-537, (Jul. 1944).

Williams, et al., "The Temperature Dependence of Relaxation Mechanisms in Amorphous Polymers and Other Glass Forming Liquids", The Journal of the American Chemical Society, 77: 3701-3707, (1955).

Wolff, et al., "Grafting Fibroblasts Genetically Modified to Produce L-Dopa in a Rat Model of Parkinson Disease", Proc. Nat'l Acad. Sci., USA, 86:9011-9014, (Nov. 1989).

Xi, et al., "Amphotericin B Treatment Dissociates in Vivo Replication of the Scrapie Agent From PrP Acummulation", Nature, 356:598-601, (Apr. 1992).

York, Powdered Raw Materials: Characterizing Batch Uniformity, Respiratory Drug Delivery IV, Programs and Proceedings, edited by Byron, Dalby and Farr, pp. 83-91, (1994).

Yoshida, et al., Clin. Res., "Paraprotein Immunoglobulins and Anti-RNA-Protein Autoantibodies", 35(2), 563A, (Mar. 1987).

Yoshinari, et al., "Moisture Induced Polymorphic Transition of Mannitol and its Morphological Transformation", International Journal of Pharmaceutics, 247:69-77, (2002).

Yoshioka, et al., "Crystallisation of Indomethacin From the Amorphous State Below and Above Its Glass Transition Membrane," Journal of Pharmaceutical Sciences, 83(12):1700-1705, (Dec. 1994).

Zubay, G. Biochemistry, Second Edition, pp. 39 & 169, Table 5-6 Major Steroid Hormones, (1988).

Zubay, G. Biochemistry, Second Edition, pp. 216-232 "Structural Properties of DNA", (1988).

Nektar U.S. Appl. No. 08/044,358, "Compositions and Methods For Nucleic Acid Delivery To The Lung" filed by Patton, et al. on Apr. 7, 1993, assigned to Inhale Therapeutic Systems.

\* cited by examiner

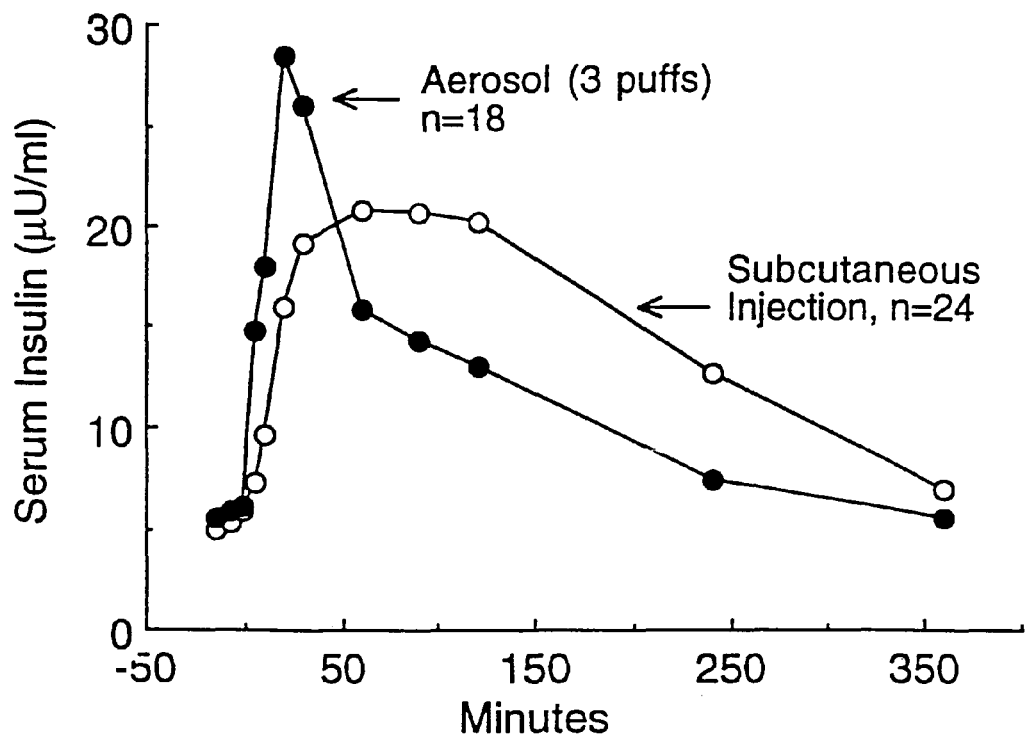
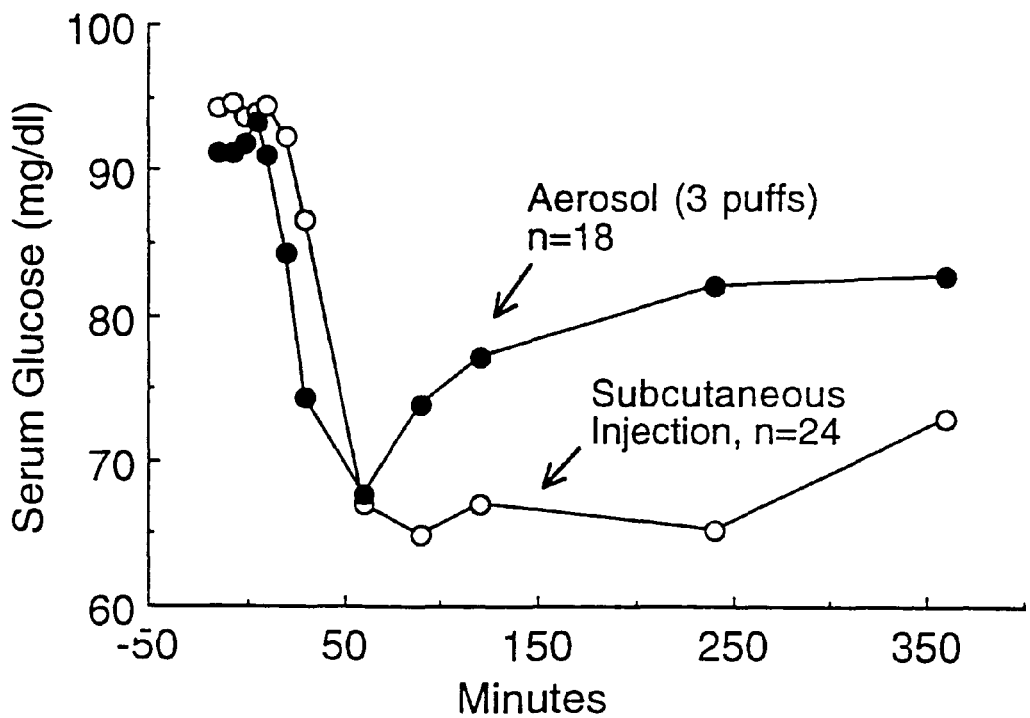

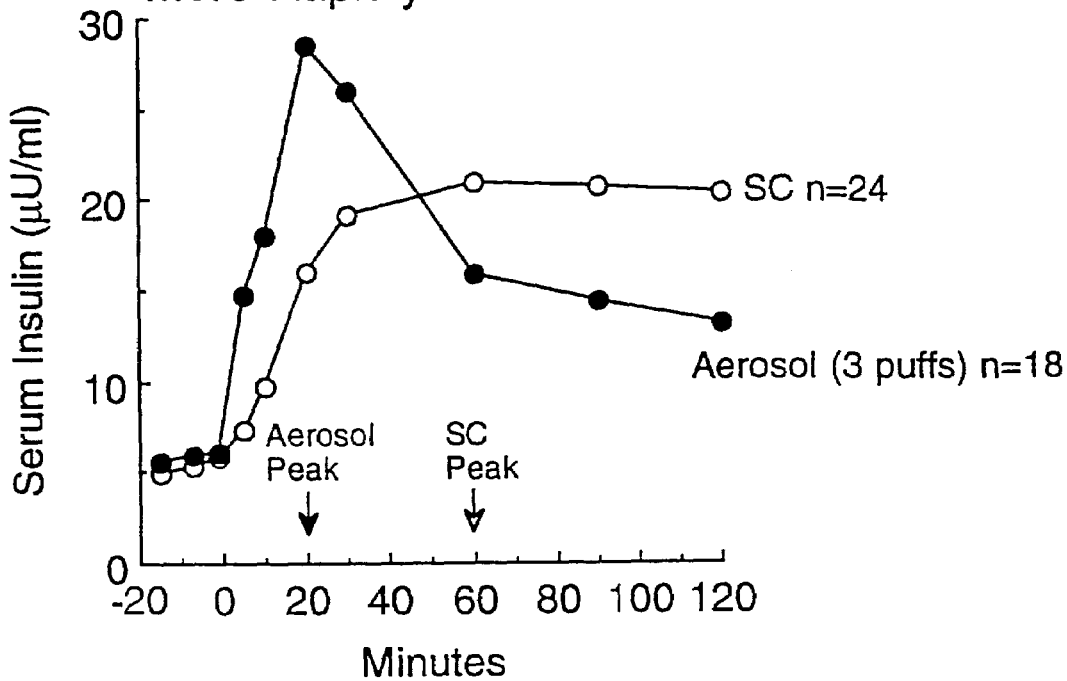
Figure 6A - Aerosol Insulin is More Rapidly Absorbed in Humans
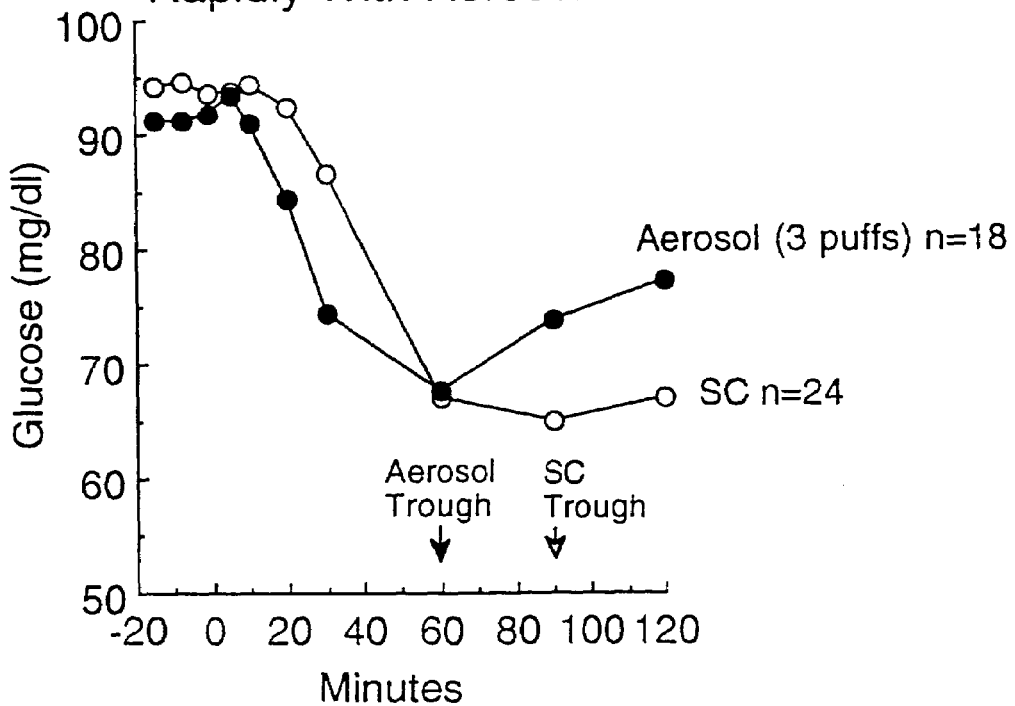
Figure 6B Serum Glucose Falls More Rapidly With Aerosol Insulin in Humans

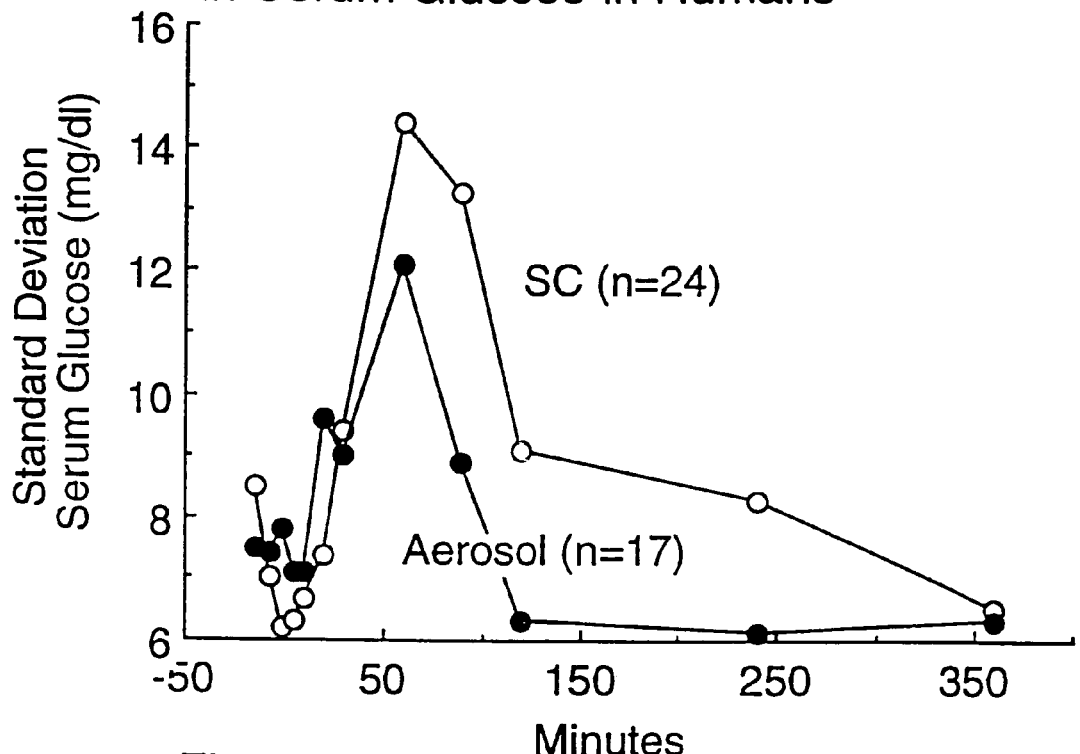
Figure 7A - Intersubject Variation in Serum Glucose in Humans
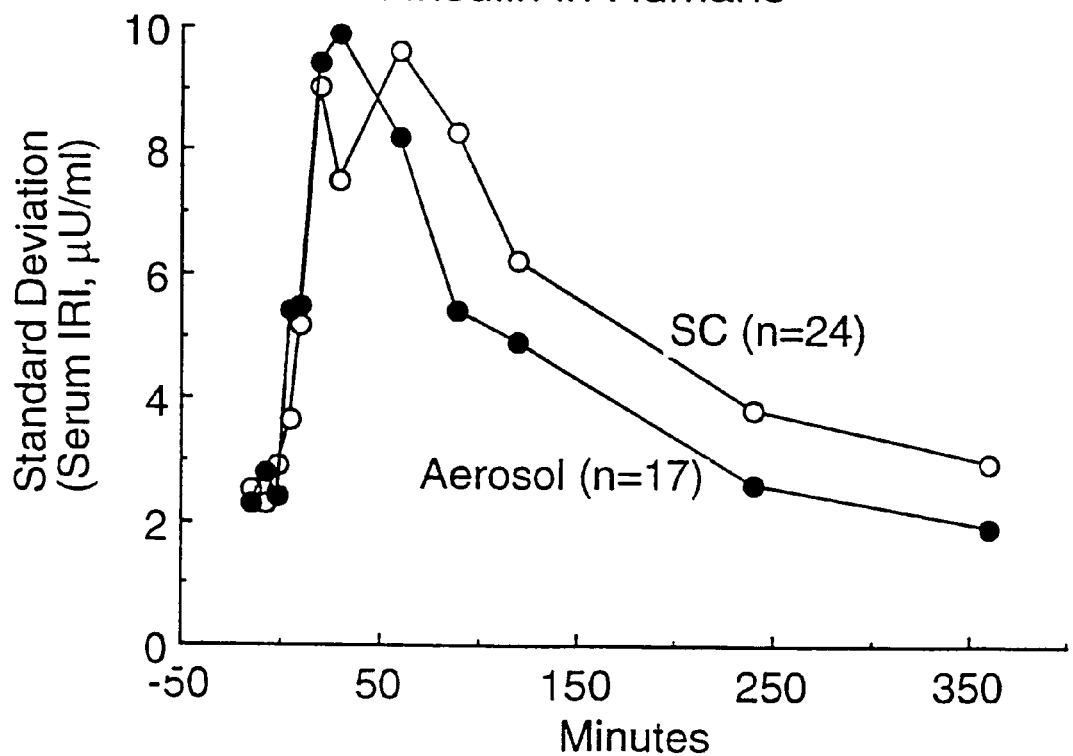
Figure 7B - Intersubject Variability in Serum Insulin in Humans

METHODS AND COMPOSITIONS FOR PULMONARY DELIVERY OF INSULIN

This application is a continuation of U.S. patent application Ser. No. 08/668,036 filed on Jun. 17, 1996 now U.S. Pat. No. 6,685,967, which is a divisional of U.S. patent application Ser. No. 08/383,475 filed on Feb. 1, 1995, now abandoned, which is a continuation-in-part of U.S. patent application 08/207,472 filed on Mar. 7, 1994, now abandoned, the full disclosures of all of the above applications being incorporated herein by reference.

BACKGROUND OF THE INVENTION

1. Field of the Invention

The present invention relates generally to methods and compositions for the respiratory delivery of insulin to diabetic patients. More particularly, the present invention relates to the pulmonary delivery of dry powder insulin preparations for rapid systemic absorption through the lungs.

Insulin is a 50 amino acid polypeptide hormone having a molecular weight of about 6,000 which is produced in the pancreatic β-cells of normal (non-diabetic) individuals. Insulin is necessary for regulating carbohydrate metabolism by reducing blood glucose levels, and a systemic deficiency causes diabetes. Survival of diabetic patients depends on the frequent and long-term administration of insulin to maintain acceptable blood glucose levels.

Insulin is most commonly administered by subcutaneous injection, typically into the abdomen or upper thighs. In order to maintain acceptable blood glucose levels, it is often necessary to inject insulin at least once or twice per day, with supplemental injections of rapid-acting insulin being administered when necessary. Aggressive treatment of diabetes can require even more frequent injections, where the patient closely monitors blood glucose levels using home diagnostic kits. The present invention is particularly concerned with the administration of rapid acting insulins which are able to provide serum insulin peaks within one hour and glucose troughs within 90 minutes.

The administration of insulin by injection is undesirable in a number of respects. First, many patients find it difficult and burdensome to inject themselves as frequently as necessary to maintain acceptable blood glucose levels. Such reluctance can lead to non-compliance, which in the most serious cases can be life-threatening. Moreover, systemic absorption of insulin from subcutaneous injection is relatively slow, frequently requiring from 45 to 90 minutes, even when fast-acting insulin formulations are employed. Thus, it has long been a goal to provide alternative insulin formulations and routes of administration which avoid the need for self-injection and which can provide rapid systemic availability of the insulin.

A variety of such alternative insulin administration roots have been proposed, including intranasal, intrarectal, and intravaginal.

While these techniques avoid the discomfort and poor compliance associated with subcutaneous injection, they each suffer from their own limitations. Intrarectal and intravaginal are inconvenient, uncomfortable, and the latter is not available to the entire population of diabetics. Intranasal delivery would be convenient and probably less objectionable than injection, but requires the use of potentially toxic "penetration enhancers" to effect passage of insulin across the nasal mucosa, which is characterized by a thick epithelial layer which is resistant to the passage of macromolecules. Of particular interest to the present invention is pulmonary insulin delivery where a patient inhales an insulin formulation and systemic absorption occurs through the thin layer of epithelial cells in the alveolar regions of the lung. Such pulmonary insulin delivery appears to provide more rapid systemic availability than does subcutaneous injection and avoids the use of a needle. Pulmonary insulin delivery, however, has yet to achieve widespread acceptance. Heretofore, pulmonary delivery has been most often accomplished through nebulization of liquid insulin formulations, requiring the use of cumbersome liquid nebulizers. Moreover, the aerosols formed by such nebulizers have a very low insulin concentration, necessitating a large number of inhalations to provide an adequate dosage. Insulin concentration is limited due to the low solubility of insulin in suitable aqueous solutions. In some cases, as many as 80 or more breaths may be required to achieve an adequate dosage, resulting in an administration time from 10 to 20 minutes, or more.

It would be desirable to provide improved methods and compositions for the pulmonary delivery of insulin. It would be particularly desirable if such methods and compositions were sufficiently convenient to permit self-administration even away from home and were able to deliver a desired total dosage with a relatively low number of breaths, preferably fewer than ten. Such methods and compositions should also provide for rapid systemic absorption of the insulin, preferably reaching a serum peak within 45 minutes or less and a resulting glucose trough within about one hour or less. Such rapid acting formulations will preferably be suitable for use in aggressive treatment protocols where injection of intermediate and long-acting insulin can be reduced or eliminated. The compositions of the present invention should also be stable, preferably consisting of a concentrated dry powder formulation.

2. Description of the Background Art

The respiratory delivery of aerosolized aqueous insulin solutions is described in a number of references, beginning with Gänsslen (1925) *Klin. Wochenschr.* 4:71 and including Laube et al. (1993) *JAMA* 269:2106–21–9; Elliott et al. (1987) *Aust. Paediatr. J.* 23:293–297; Wigley et al. (1971) *Diabetes* 20:552–556. Corthorpe et al. (1992) *Pharm Res* 9:764–768; Govinda (1959) *Indian J. Physiol. Pharmacol.* 3:161–167; Hastings et al. (1992) *J. Appl. Physiol.* 73:1310–1316; Liu et al. (1993) *JAMA* 269:2106–2109; Nagano et al. (1985) *Jikeikai Med. J.* 32:503–506; Sakr (1992) *Int. J. Phar.* 86:1–7; and Yoshida et al. (1987) *Clin. Res.* 35:160–166. Pulmonary delivery of dry powder medicaments, such as insulin, in a large particle carrier vehicle is described in U.S. Pat. No. 5,254,330. A metered dose inhaler (MDI) for delivering crystalline insulin suspended in a propellant is described in Lee and Sciara (1976) *J. Pharm. Sci.* 65:567–572. A MDI for delivering insulin into a spacer for regulating inhalation flow rate is described in U.S. Pat. No. 5,320,094. The intrabronchial administration of recombinant insulin is briefly described in Schlüter et al. (Abstract) (1984) *Diabetes* 33:75A and Köhler et al. (1987) *Atemw. Lungenkrkh.* 13:230–232. Intranasal and respiratory delivery of a variety of polypeptides, including insulin, in the presence of an enhancer, are described in U.S. Pat. No. 5,011,678 and Nagai et al. (1984) *J. Contr. Rel.* 1:15–22. Intranasal delivery of insulin in the presence of enhancers and/or contained in controlled release formulations are described in U.S. Pat. Nos. 5,204,108; 4,294,829; and 4,153,689; PCT Applications WO 93/02712, WO 91/02545, WO 90/09780, and WO 88/04556; British Patent 1,527,605; Rydén and Edman (1992) *Int. J. Pharm.* 83:1–10; and Björk and Edman (1988) *Int. J. Pharm.* 47:233–238. The preparation and stability of amorphous insulin were described by Rigsbee and Pikal at the American Association of Pharmaceutical Sciences (AAPS), Nov. 14–18, 1993, Lake Buena Vista, Fla. Methods for spray drying polypeptide, polynucleotide and other labile drugs in a carrier which forms an amorphous structure which stabilize the drug are described in European patent application 520 748.

SUMMARY OF THE INVENTION

According to the present invention, methods and compositions for the aerosolization and systemic delivery of insulin to a mammalian host, particularly a human patient suffering from diabetes, provide for rapid absorption into blood circulation while avoiding subcutaneous injection. In particular, the methods of the present invention rely on pulmonary delivery of insulin in the form of a dry powder. Surprisingly, it has been found that inhaled dry insulin powders are deposited in the alveolar regions of the lung and rapidly absorbed through the epithelial cells of the alveolar region into blood circulation. Thus, pulmonary delivery of insulin powders can be an effective alternative to administration by subcutaneous injection.

In a first aspect of the present invention, insulin is provided as a dry powder, usually but not necessarily in a substantially amorphous state, and dispersed in an air or other physiologically acceptable gas stream to form an aerosol. The aerosol is captured in a chamber having a mouthpiece, where it is available for a subsequent inhalation by a patient. Optionally, the dry powder insulin is combined with a pharmaceutically acceptable dry powder carrier, as described in more detail below. The insulin powder preferably comprises particles having a diameter less then 10 µm, more preferably less than 7.5 µm, and most preferably below 5 µm, usually being in the range from 0.1 µm to 5 µm. Surprisingly, it has been found that the dry powder insulin compositions of the present invention are absorbed in the lung without the use of penetration enhancers such as those required for absorption through the nasal mucosa and upper respiratory tract.

In a second aspect, the present invention provides insulin compositions consisting essentially of dry powder insulin having an average particle size below 10 µm which may be combined with dry powder pharmaceutical carriers. The insulin composition is preferably free from penetration enhancers and comprises particles having a diameter less than 10 µm, preferably less than 7.5 µm, and most preferably below 5 µm, usually being in the range from 0.1 µm to 5 µm. Usually, the insulin dry powder will have from 5% to 99% by weight insulin in the composition, more usually from 15% to 80%, in a suitable pharmaceutical carrier, usually a carbohydrate, an organic salt, an amino acid, peptide, or protein, as described in more detail hereinafter.

In a third aspect of the present invention, insulin dry powders are prepared by dissolving insulin in an aqueous buffer to form a solution and spray drying the solution to produce substantially amorphous particles having a particle size less than 10 µm, preferably less than 7.5 µm, and most preferably below 5 µm, usually being in the range from 0.1 µm to 5 µm. Optionally, the pharmaceutical carrier is also dissolved in the buffer, to form a homogeneous solution, wherein spray drying of the solution produces individual particles comprising insulin, carrier buffer, and any other components which were present in the solution. Preferably the carrier is a carbohydrate, organic salt, amino acid, peptide, or protein which produces a substantially amorphous structure upon spray drying. The amorphous carrier may be either glassy or rubbery and enhances stability of the insulin during storage. Advantageously, such stabilized formulations are also able to effectively deliver insulin to the blood stream upon inhalation to the alveolar regions of the lungs.

A further understanding of the nature and advantages of the invention will become apparent by reference to the remaining portions of the specification and drawings.

BRIEF DESCRIPTION OF THE DRAWINGS

FIG. 5A is a graph illustrating the mean insulin concentration over time for subcutaneous injection (○) and for inhalation of three puffs ( ) in humans.

FIG. 5B shows the mean glucose concentration corresponding to the insulin concentrations of FIG. 5A.

FIG. 6A is a graph illustrating serum insulin concentration over time as a result of subcutaneous injection (○) and three puffs of aerosol administration (●) in humans.

FIG. 6B is a graph illustrating the serum glucose levels corresponding to the insulin levels in FIG. 6A.

FIGS. 7A and 7B provide a comparison of the intersubject variability of serum insulin (7A) and glucose levels (7B) for subcutaneous administration (○) and aerosol administration (●).

FIG. 8A is a chromatograph of an insulin standard stressed in 10 mM HCl at 25° C., showing human insulin eluting at 23.87 minutes desamido insulin eluting at 30.47 minutes. FIG. 8B shows a similar chromatogram of a human insulin standard. FIG. 8C shows a similar chromatogram of reconstituted, spray-dried insulin formulation prepared according to the present invention.

DETAILED DESCRIPTION OF SPECIFIC EMBODIMENTS

Figure 1:
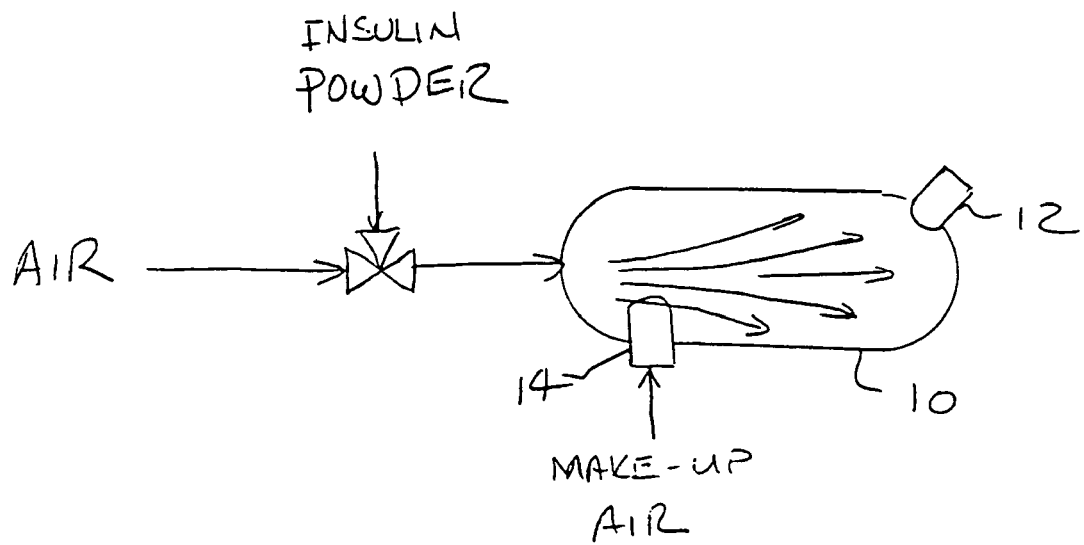
FIG. 1 is a schematic illustration of a system for aerosolizing a dose of insulin according to the method of the present invention.
Figure 2:
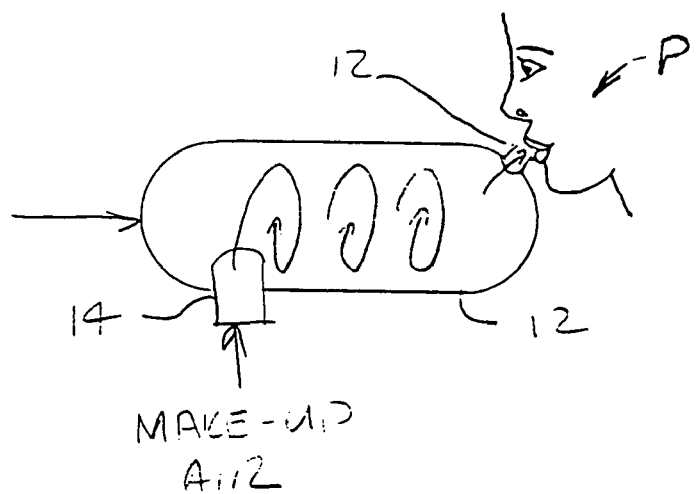
FIG. 2 is a schematic illustration of a patient inhaling an aerosolized dose of insulin from the system of FIG. 1.

According to the present invention, insulin is provided as a dry power. By "dry powder" it is meant that the moisture content of the powder is below about 10% by weight, usually below about 5% by weight, and preferably being below about 3% by weight. By "powder," it is meant that the insulin comprises free flowing particulates having a size selected to permit penetration into the alveoli of the lungs, preferably being less than 10 µm in diameter, preferably less than 7.5 µm, and most preferably less than 5 µm, and usually being in the range from 0.1 µm to 5 µm in diameter.

The present invention is based at least in part on the unexpected observation that dry powder insulins are readily and rapidly absorbed through the lungs of a host. It was surprising that dry powder insulins could reach the alveolar region of the lungs, as water-soluble drugs such as insulin particles are known to be hygroscopic. See, e.g. Byron, ed., *Respiratory Drug Delivery*, CRC Press, Boca Raton (1990), p. 150. Thus, it would have been expected that as the particles passed through the airways of the lung (which has a relative humidity in excess of 99% at 37° C.), the individual particles would have a tendency to absorb water and grow to an effective particle size larger than the 10 µm upper limit of the present invention. If a substantial fraction of the insulin particles were larger than the target size range, it would be expected that the particles would deposit within the central airways of the lungs rather than the alveolar region, thus limiting delivery and subsequent systemic absorption. Moreover, the fluid layer over the epithelial cells of the lungs is very thin, usually a fraction of the diameter of the insulin powders being delivered. Thus, it was unpredictable prior to the present invention whether the dry insulin particles would dissolve upon deposition within the alveolar regions of the lungs. Surprisingly, the dry insulin powders are apparently able to both penetrate into the alveolar regions of the lungs and dissolve once they have deposited within the alveolar region of the lung. The dissolved insulin is then able to cross the epithelial cells into circulation.

It is presently believed that the effective absorption of insulin results from a rapid dissolution in the ultrathin (<0.1 µm) fluid layer of the alveolar lining. The particles of the present invention thus have a mean size which is from 10 to 50 times larger than the lung fluid layer, making it unexpected that the particles are dissolved and the insulin systemically absorbed in a rapid manner. Indeed, as shown in the Experimental section hereinafter, the dry insulin formulations of the present invention can provide even more rapid serum insulin peaks and glucose troughs than afforded by subcutaneous injection, which is presently the most common form of administration. An understanding of the precise mechanism, however, is not necessary for practicing the present invention as described herein.

Preferred compositions according to the present invention will be substantially free from penetration enhancers. "Penetration enhancers" are surface active compounds which promote penetration of insulin (or other drugs) through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. Surprisingly, it has been found that the dry powder insulin compositions of the present invention are readily absorbed in the lungs without the need to employ penetration enhancers.

Insulin dry powders suitable for use in the present invention include amorphous insulins, crystalline insulins, and mixtures of both amorphous and crystalline insulins. Dry powder insulins are preferably prepared by spray drying under conditions which result in a substantially amorphous powder having a particle size within the above-stated range. Alternatively, amorphous insulins could be prepared by lyophilization (freeze-drying), vacuum drying, or evaporative drying of a suitable insulin solution under conditions to produce the amorphous structure. The amorphous insulin so produced can then be ground or milled to produce particles within the desired size range. Crystalline dry powder insulins may be formed by grinding or jet milling of bulk crystalline insulin. The preferred method for forming insulin powders comprising particulates in the desired size range is spray drying, where pure, bulk insulin (usually in a crystalline form) is first dissolved in a physiologically acceptable aqueous buffer, typically a citrate buffer having a pH in the range from about 2 to 9. The insulin is dissolved at a concentration from 0.01% by weight to 1% by weight, usually from 0.1% to 0.2%. The solutions may then be spray dried in conventional spray drying equipment from commercial suppliers, such as Buchi, Niro, and the like, resulting in a substantially amorphous particulate product.

The dry insulin powders may consist essentially of insulin particles within the requisite size range and be substantially free from any other biologically active components, pharmaceutical carriers, and the like. Such "neat" formulations may include minor components, such as preservatives, present in low amounts, typically below 10% by weight and usually below 5% by weight. Using such neat formulations, the number of inhalations required for even high dosages can be substantially reduced, often to only a single breath.

The insulin powders of the present invention may optionally be combined with pharmaceutical carriers or excipients which are suitable for respiratory and pulmonary administration. Such carriers may serve simply as bulking agents when it is desired to reduce the insulin concentration in the powder which is being delivered to a patient, but may also serve to enhance the stability of the insulin compositions and to improve the dispersability of the powder within a powder dispersion device in order to provide more efficient and reproducible delivery of the insulin and to improve handling characteristics of the insulin such as flowability and consistency to facilitate manufacturing and powder filling.

Suitable carrier materials may be in the form of an amorphous powder, a crystalline powder, or a combination of amorphous and crystalline powders. Suitable materials include carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamine hydrochloride, and the like; (d) peptides and proteins, such as aspartame, human serum albumin, gelatin, and the like; (e) alditols, such as mannitol, xylitol, and the like. A preferred group of carriers includes lactose, trehalose, raffinose, maltodextrins, glycine, sodium citrate, tromethamine hydrochloride, human serum albumin, and mannitol.

Such carrier materials may be combined with the insulin prior to spray drying, i.e., by adding the carrier material to the buffer solution which is prepared for spray drying. In that way, the carrier material will be formed simultaneously with and as part of the insulin particles. Typically, when the carrier is formed by spray drying together with the insulin, the insulin will be present in each individual particle at a weight percent in the range from 5% to 95%, preferably from 20% to 80%. The remainder of the particle will primarily be carrier material (typically being from 5% to 95%, usually being from 20% to 80% by weight), but will also include buffer(s) and may include other components as described above. The presence of carrier material in the particles which are delivered to the alveolar region of the lung (i.e., those in the requisite size range below 10 µm) has been found not to significantly interfere with systemic absorption of insulin.

Alternatively, the carriers may be separately prepared in a dry powder form and combined with the dry powder insulin by blending. The separately prepared powder carriers will usually be crystalline (to avoid water absorption), but might in some cases be amorphous or mixtures of crystalline and amorphous. The size of the carrier particles may be selected to improve the flowability of the insulin powder, typically being in the range from 25 μm to 100 μm. Carrier particles in this size range will generally not penetrate into the alveolar region of the lung and will often separate from the insulin in the delivery device prior to inhalation. Thus, the particles which penetrate into the alveolar region of the lung will consist essentially of insulin and buffer. A preferred carrier material is crystalline mannitol having a size in the above-stated range.

The dry insulin powders of the present inventions may also be combined with other active components. For example, it may be desirable to combine small amounts of amylin or active amylin analogues in the insulin powders to improve the treatment of diabetes. Amylin is a hormone which is secreted with insulin from the pancreatic cells in normal (non-diabetic) individuals. It is believed that amylin modulates insulin activity in vivo, and it has been proposed that simultaneous administration of amylin with insulin could improve blood glucose control. Combining dry powder amylin with insulin in the compositions of the present invention will provide a particularly convenient product for achieving such simultaneous administration. Amylin may be combined with insulin at from 0.1% by weight to 10% by weight (based on the total weight of insulin in a dose), preferably from 0.5% by weight to 2.5% by weight. Amylin is available from commercial suppliers, such as Amylin Corporation, San Diego, Calif., and can be readily formulated in the compositions of the present invention. For example, amylin may be dissolved in aqueous or other suitable solutions together with the insulin, and optionally carriers, and the solution spray dried to produce the powder product.

The dry powder insulin compositions of the present invention are preferably aerosolized by dispersion in a flowing air or other physiologically acceptable gas stream in a conventional manner. One system suitable for such dispersion is described in copending application Ser. No. 07/910,048, which has been published as WO 93/00951, the full disclosures of which are incorporated herein by reference. Referring to FIG. 1 herein, dry, free-flowing insulin powder is introduced into a high velocity air or gas stream, and the resulting dispersion introduced into a holding chamber 10. The holding chamber 10 includes a mouthpiece 12 at an end opposite to the entry point of the air powder dispersion. The volume of the chamber 10 is sufficiently large to capture a desired dose and may optionally have baffles and/or one-way valves for promoting containment. After a dose of the insulin powder has been captured in chamber 10, a patient P (FIG. 2) inhales on the mouthpiece 12 to draw the aerosolized dispersion into his lungs. As the patient P inhales, make-up air is introduced through a tangentially oriented air inlet port 14, whereby the air flows in a generally vortical pattern to sweep the aerosolized insulin from the chamber into the patient's lungs. The volume of the chamber and the aerosolized dose are such that a patient is able to completely inhale the entire aerosolized insulin dose followed by sufficient air to ensure that the insulin reaches the lower alveolar regions of the lung.

Such aerosolized insulin powders are particularly useful in place of subcutaneous injections of rapid acting insulin in the treatment of diabetes and related insulin-deficiencies. Surprisingly, it has been found that the aerosol administration of dry powder insulin results in significantly more rapid insulin absorption and glucose response than is achieved by subcutaneous injection. Thus, the methods and compositions of the present invention will be particularly valuable in treatment protocols where a patient monitors blood glucose levels frequently and administers insulin as needed to maintain a target serum concentration, but will also be useful whenever systemic insulin administration is required. The patient can achieve a desired dosage by inhaling an appropriate amount of insulin, as just described. The efficiency of systemic insulin delivery via the method as just described will typically be in the range from about 15% to 30%, with individual dosages (on a per inhalation basis), typically being in the range from about 0.5 mg to 10 mg. Usually, the total dosage of insulin desired during a single respiratory administration will be in the range from about 0.5 mg to 15 mg. Thus, the desired dosage may be effective by the patient taking from 1 breath to 4 breaths.

The following examples are offered by way of illustration, not by way of limitation.

EXPERIMENTAL

Materials and Methods

Materials

Crystalline human zinc insulin, 26.3 Units/mg, (Lilly Lot #784KK2) was obtained from Eli Lilly and Company, Indianapolis, Ind. and found to be >99% pure as measured by rpHPLC. USP mannitol was obtained from Roquette Corporation (Gurnee, Ill.). Raffinose was purchased from Pfanstiehl Laboratories (Waukegan, Ill.). Sodium citrate dihydrate, USP, ACS and citric acid monohydrate USP were obtained from J.T. Baker (Phillipsburg, N.J.).

Powder Production

Insulin powders were made by dissolving bulk crystalline insulin in sodium citrate buffer containing excipient (mannitol, or raffinose, or none) to give final solids concentration of 7.5 mg/ml and a pH of 6.7±0.3. The spray dryer was operated with an inlet temperature between 110° C. to 120° C. and a liquid feed rate of 5 ml/min, resulting in an outlet temperature between 70° C. and 80° C. The solutions were then filtered through a 0.22 μm filter and spray dried in a Buchi Spray Dryer to form a fine white amorphous powder. The resulting powders were stored in tightly capped containers in a dry environment (<10% RH).

Powder Analyses

The particle size distribution of the powders was measured by liquid centrifugal sedimentation in a Horiba CAPA-700 Particle Size Analyzer following dispersion of the powders in Sedisperse A-11 (Micromeritics, Norcross, Ga.). The moisture content of the powders was measured by the Karl Fischer technique using a Mitsubishi CA-06 Moisture Meter.

The integrity of insulin before and after powder processing was measured against a reference standard of human insulin by redissolving weighed portions of powder in distilled water and comparing the redissolved solution with the original solution put into the spray dryer. Retention time and peak area by rpHPLC were used to determine whether the insulin molecule had been chemically modified or degraded in process. UV absorbance was used to determine insulin concentration (at 278 nm) and presence or absence of insoluble aggregates (at 400 nm). In addition, the pHs of the starting and reconstituted solutions were measured. The amorphous nature of the insulin powder was confirmed by polarizing light microscopy.

Rat Aerosol Exposures

Rat experiments were conducted in an aerosol exposure room. Female rats (280–300 gm) were fasted overnight. Animals (21–24/experiment) were placed in Plexiglas tubes and mounted into a 48 port, nose-only aerosol exposure chamber (In-Tox Products, Albuquerque, N. Mex.). Airflow to the breathing zone was maintained at 7.2–9.8 liters/minute and removed by vacuum so that there was a slight negative pressure (~1.5 cm $H_2O$) in the chamber as measured by a magnahelic gauge. Aerosol exposure times were between 5–20 minutes depending on how much powder was fed into the chamber. Powders were fed by hand into a small Venturi nozzle which dispersed the powder particles to form a fine aerosol cloud. The Venturi nozzle was operated at a pressure in excess of 15 psig, and the air flow was set at 7.2 l/min to 9.8 l/min. The Venturi nozzle was fitted into the bottom of a clear Plexiglas dispersion chamber (750 ml) which passed the aerosol directly into a nose-only exposure chamber.

Rat Aerosol Chamber Calibration

The concentration of the powder at the breathing zone was measured by taking multiple, timed filter samples at the breathing zone with In-Tox filter holders at a vacuum flow of 2 liters/min. The chamber was calibrated both with and without animals. Powder mass was determined gravimetrically. The particle size of the powders at the breathing zone was measured with cascade impactor (In Tox Products) placed at a breathing hole and operated at a flow of 2 liters/min. Powder mass on each stage was determined gravimetrically.

Each powder test utilized 21–24 rats and the aerosol exposures lasted 5–20 minutes. Three rats were killed at 0 time and then at ~7, 15, 30, 60, 90, 120, 180, and 240 minutes after the termination of the aerosol exposure. Animals were anesthetized, their abdomens opened, and a large blood sample was drawn from the ventral aorta. The animals were then killed by cervical dislocation.

Blood was allowed to clot at room temperature for 30 minutes and then centrifuged for 20 minutes at 3500 rpm in serum separator tubes. Serum was either analyzed immediately or frozen at −80° C. until analysis. As soon as possible (0–7 min) after the termination of the aerosol dosing, 3 rats were killed, their blood drawn and their lungs lavaged with six 5 ml rinses of phosphate buffered saline (PBS). The amount of insulin in the final pooled lavage sample was used as the aerosol dose for the rat in calculations of bioavailability.

Primate Exposure System

Young, wild-captured, male cynomolgus monkeys strain *Macaca fascicularis* (2–5 kg) (Charles River Primates, Inc.) were used for the primate aerosol studies (3–4 animals/group). The animals were either subcutaneously injected with Humulin (Eli Lilly, Indianapolis, Ind.) or exposed to a powder aerosol of insulin. Each animal was placed in a head-only exposure unit to provide a fresh supply of the test atmosphere at an adequate flow rate (7 L/min) to provide minimum oxygen requirements of the animal. The animals were restrained in a chair-like apparatus which placed them in an upright sitting position. The hoods were clear allowing the animals complete visualization of their environment. An indwelling catheter was placed in the leg so that blood samples could be taken at any time. The monkeys were fully awake during the whole procedure and appeared to be calm. Primate blood was treated the same as rat (see above).

The primate aerosol exposure system included a breath monitor that allowed quantification of the amount of air inhaled by each monkey. This value, coupled with measurements of the concentration of insulin in the inspired air allowed the calculation of exactly how much insulin was inhaled by each animal.

Human Trials

Insulin was administered to 24 normal human subjects subcutaneously as well as by inhalation of aerosolized dry insulin powders. Each subcutaneous injection consisted of 10.4U of Humulin R, 100 U/ml (Eli Lilly, Indianapolis, Ind.). The dry insulin powders were amorphous and prepared by spray drying as described above with 20% by weight mannitol excipient. Doses (5 mg) of the insulin dry powder were dispersed in a high-velocity air stream to produce a fine aerosol that was captured in a chamber. Each subject inhaled the aerosol powder by taking a slow, deep breath of each aerosol bolus or "puff." Powder was administered in three puffs (for a dosage of 31.9U). Serum insulin and glucose levels were determined over time, as described below.

Serum Assays

Serum insulin levels in rats, primates, and humans were determined using Coat-A-Count radio immunoassay kits for human insulin (Diagnostic Products Corporation, Los Angeles, Calif.). Standard curves were run with every batch of samples. The sensitivity of the assay was approximately 43 pg/ml. The within assay variability (% CV) is <5%. Glucose assays were performed by California Veterinary Diagnostics, Inc. in West Sacramento, Calif. using the Glucose/HK Reagent System Pack for the Boehringer Mannheim/Hitachi 747 Analyzer. The within assay variability (% CV) is <3%.

In the rate experiments, relative bioavailabilities of the aerosol were calculated by comparing the dose adjusted, immunoreactive insulin (IRI) area under the curve (AUC) of the concentration-time profile with that obtained from subcutaneous injection. In rats the total lavaged insulin mass was used as the aerosol dose. Some insulin is absorbed before the lungs can be lavaged so the dose estimated by this technique is probably a slight underestimate of the total deposited dose. No corrections for this presumed loss were made.

In the monkey experiments, relative bioavailabilities were calculated similar to the rats above except that instead of using lavaged lung insulin as the aerosol dose, the total amount of insulin inhaled was used. In the rats, only material deposited in the lungs, not insulin deposited in the nasal passages and throat, was included in the dose estimate. In the monkeys, all insulin that entered the animals was included in the dose estimate.

Results of Insulin Absorption in Rats

Figure 8A:
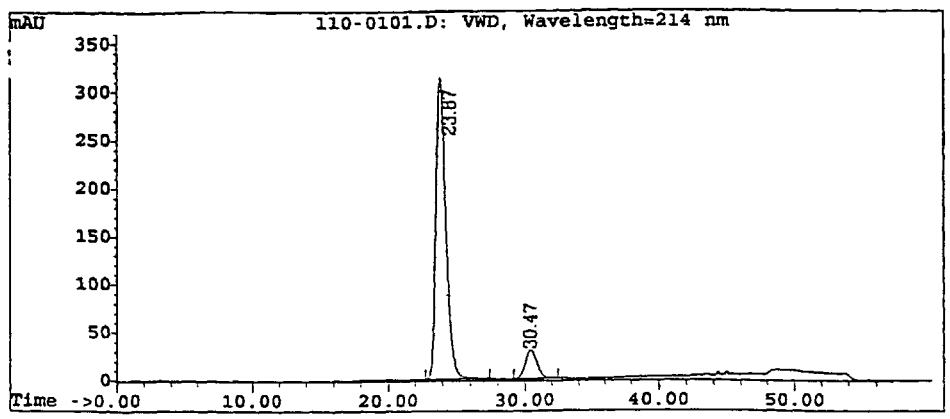
FIGS. 8A, 8B, and 8C show rpHPLC chromatograms of a human insulin.
Figure 8B:
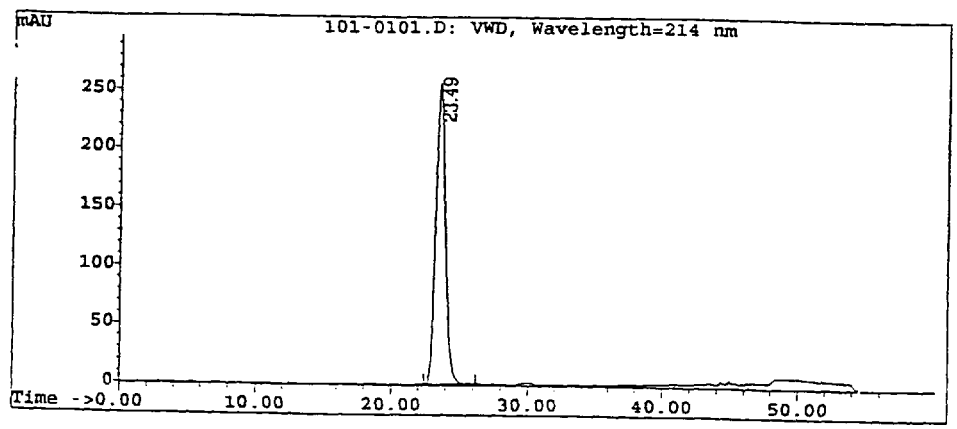
Figure 8C:
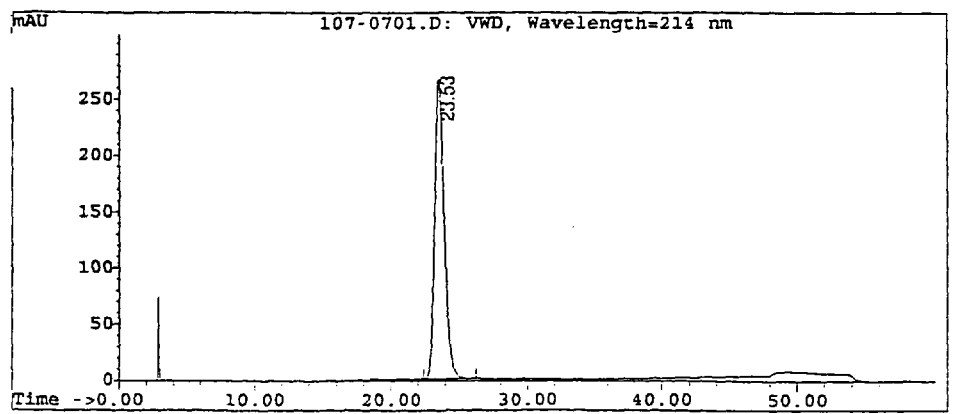
Figure 9:
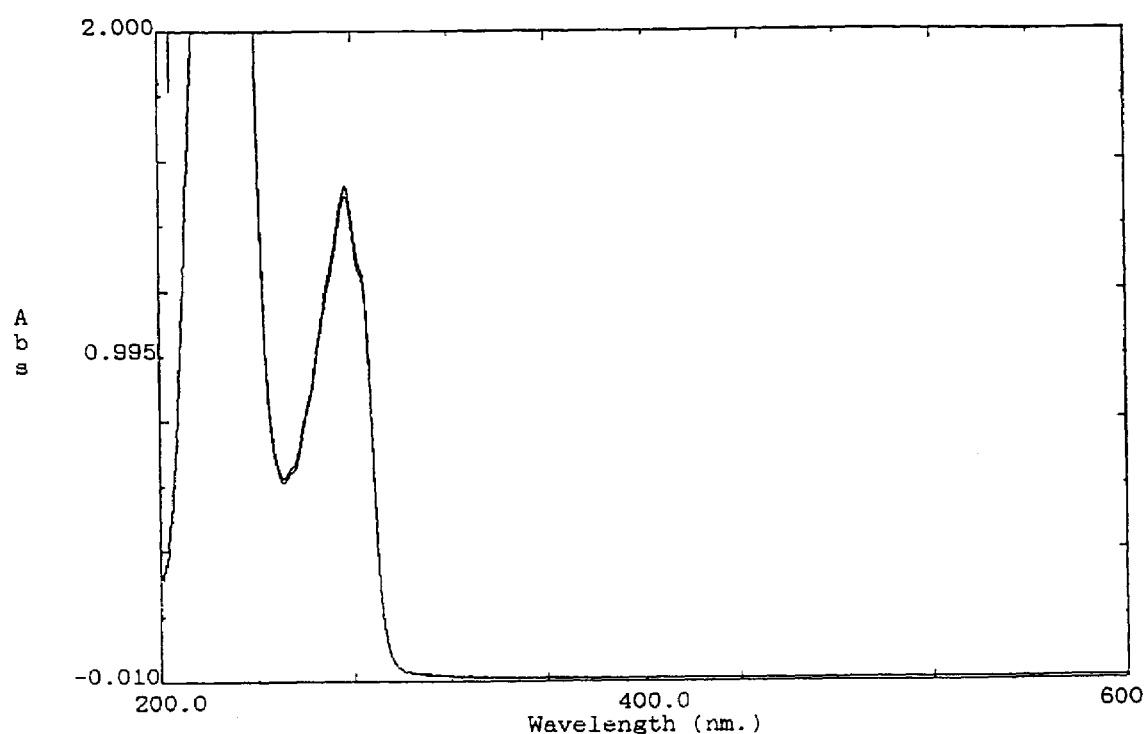
FIG. 9 shows an ultraviolet spectra of an insulin formulation before and after spray drying. No light scattering was observed in the visible spectrum, indicating that insulin did not aggregate during the spray drying process.

All of the insulin powders used in the animal studies had particle sizes (mass median diameters) ranging between 1–3 μm and moisture contents <3%. The insulin purity of the powders as measured by rpHPLC was >97%. Representative chromatographs of the 20% insulin formulation are shown in FIG. 8C. The powders yielded a clear solution upon reconstitution with pure water with an ultraviolet absorbance value <0.01 at 400 nm and a pH of 6.7±0.3. Representative ultraviolet (UV) spectra for the 20% insulin formulation are shown in FIG. 9.

The following three insulin powder formulations were tested in rats as aerosols in the In-Tox 48 port, exposure chamber.

1. 87.9% insulin; 11.5% sodium citrate; 0.6% citric acid.

2. 20% insulin; 66% mannitol: 12.4% sodium citrate: 0.6% citric acid.

3. 20% insulin; 66% raffinose; 12.4% sodium citrate: 0.6% citric acid.

Table 1 lists the key measurements in the three different rat exposure studies including characterizations of the aerosol at the breathing zone and chamber operating conditions. A fraction of the powder fed into the venturi nozzle reached the breathing zones of the rats (34%–67%) because of losses in the walls due to impaction and incomplete dispersion of the powder during powder feed. The particle size of the aerosol at the breathing zone, however, was ideal for pulmonary deposition (1.3–1.9 μm) and was somewhat smaller than the original formulation particle size (2.0–2.8 μm) due to selective loss of the larger particles in the animal exposure chamber.

TABLE 1

| Rat Aerosol Exposure Measurements | 88% Insulin | 20% Insulin Mannitol | 20% Insulin Raffinose |
|---|---|---|---|
| Chamber Flow Rate | 7.2 L/min | 9.6 L/min | 9.8 L/min |
| Powder Mass Median Diameter (MMD) | 2.2 μm | 2.8 μm | 2.0 μm |
| Powder Fed into Chamber | 70 mgs | 255 mgs | 260 mgs |
| Powder Feed Time | 5 min | 14 min | 20 min |
| Powder at Breathing Zone | 40 mgs | 171 mgs | 88 mgs |
| Insulin at Breathing Zone | 35 mgs | 34 mgs | 18 mgs |
| % Total Powder at Breathing Zone | 57% | 67% | 34% |
| Mass Median Aerodynamic Diameter (MAD) | 1.1 mg/L | 1.3 mg/L | 0.45 mg/L |
| Particle Size at Breathing Zone | 1.4 μm | 1.9 μm | 1.3 μm |
| Insulin Recovered in Lavage | 30.7 ± 5.2 μg | 12.7 ± 6.9 μg | 31.6 ± 12.9 μg |
| Serum Insulin AUC (ng min/ml) | 104 | 201 | 150 |

Table 2 shows the rat serum insulin and glucose results from the three aerosol and one SC study. FIGS. 3A and 3B show the serum immunoreactive insulin (IRI) concentration-time profiles and the serum glucose concentration-time profiles for the three formulations administered by aerosol. Table 3 presents the insulin $t_{max}$, and the glucose $t_{min}$ from the different studies as well as the relative bioavailability of the aerosol compared to SC injection.

TABLE 2

Serum Insulin and Glucose Results in Rats

| Formulation | Route | Time (min) | Serum Insulin (pg/ml ± 1 S.D.) n = 3 rats/ timept | Serum Glucose (mg/dl ± 1 S.D.) n = 3 rats/ timept |
|---|---|---|---|---|
| 88% Insulin | Aerosol | 0 | 230 ± 184 | 106 ± 12 |
| (Aerosol exposure | Aerosol | 12 | 1020 ± 312 | 114 ± 10 |
| completed at minute 5) | Aerosol | 21 | 165 ± 768 | 81 ± 10 |
| Av. Dose = 31 μg/rat | Aerosol | 36 | 876 ± 764 | 66 ± 7 |
| | Aerosol | 66 | 684 ± 416 | 62 ± 15 |
| | Aerosol | 96 | 568 ± 128 | 65 ± 10 |
| | Aerosol | 126 | 564 ± 260 | 73 ± 11 |
| | Aerosol | 186 | 712 ± 140 | 93 ± 5 |
| 20% Insulin-Mannitol | Aerosol | 0 | 476 ± 56 | 165 ± 18 |
| (Aerosol exposure | Aerosol | 22 | 1476 ± 428 | 117 ± 15 |
| completed at minute 14) | Aerosol | 35 | 2480 ± 892 | 101 ± 19 |
| Av. Dose = 13 μg/rat | Aerosol | 57 | 1204 ± 64 | 64 ± 13 |
| | Aerosol | 87 | 1084 ± 396 | 63 ± 17 |
| | Aerosol | 117 | 664 ± 180 | 105 ± 38 |
| | Aerosol | 147 | 1228 ± 416 | 108 ± 22 |
| | Aerosol | 207 | 676 ± 100 | 119 ± 33 |
| 20% Insulin-Raffinose | Aerosol | 0 | 426 ± 97 | 157 ± 37 |
| (Aerosol exposure | Aerosol | 27 | 2948 ± 2816 | 139 ± 46 |
| completed at minute 20) | Aerosol | 42 | 1504 ± 592 | 181 ± 11 |
| Av. Dose = 32 μg/rat | Aerosol | 57 | 1272 ± 496 | 124 ± 45 |
| | Aerosol | 87 | 852 ± 164 | 128 ± 17 |
| | Aerosol | 117 | 604 ± 156 | 124 ± 9 |
| | Aerosol | 147 | 532 ± 172 | 172 ± 12 |
| | Aerosol | 207 | 556 ± 100 | 218 ± 34 |
| 20% Insulin-Mannitol | Subcutan | 0 | 360 ± 140 | 107 ± 5 |
| Dose = 30 μg | Subcutan | 15 | 14200 ± 3160 | 53 ± 2 |
| Insulin/rat | Subcutan | 30 | 10160 ± 720 | 24 ± 5 |
| | Subcutan | 60 | 11000 ± 1080 | 28 ± 6 |
| | Subcutan | 90 | 2440 ± 1160 | 25 ± 7 |
| | Subcutan | 120 | 3520 ± 840 | 49 ± 3 |
| | Subcutan | 180 | 1280 ± 800 | 40 ± 17 |
| | Subcutan | 240 | 400 ± 260 | 77 ± 34 |

TABLE 3

A Comparison of Aerosol and Subcutaneous (SC) Insulin in Animals

|  | Rat SC | Rat Aerosol 88% Insulin | Rat Aerosol 20% Insulin Mannitol | Rat Aerosol 20% Insulin Raffinose | Monkey SC | Monkey Aerosol 20% Insulin Mannitol |
|---|---|---|---|---|---|---|
| Insulin Max* | 15 min | 16 min | 21 min | 17 min | 15 min | 30 min |
| Glucose Min.* | 30 min | 31 min | 43 min | 37 min | 45 min | 45 min |
| Glucose Drop | 77% | 42% | 62% | 21% | 45% | 73% |
| Rel Bioavail. | 100% | 10%** | 44%** | 14%** | 100% | 12%*** |

Figure 3A:
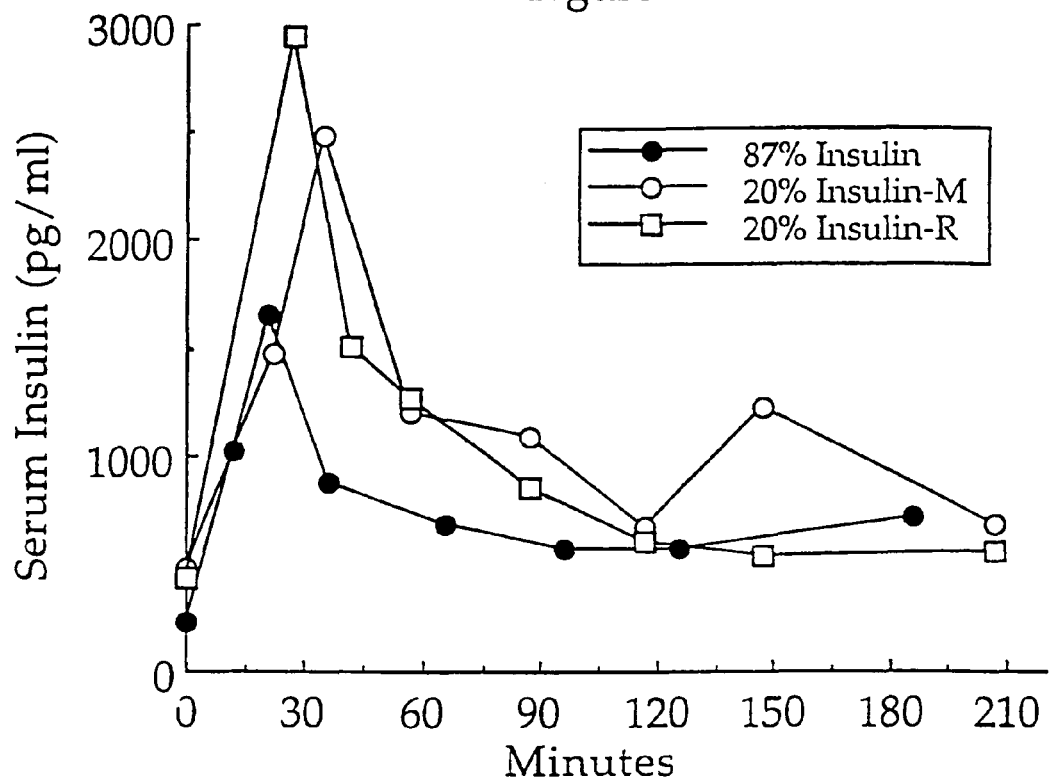
FIGS. 3A and 3B are graphs illustrating the absorption of recombinant human insulin in rats and resulting glucose response following aerosolization of three different dry powder formulations. Each point represents the mean value from three different rats. At zero time, the dry powder aerosol generator was turned on. Aerosolization was complete at 5 min, 14 min and 20 min for the 87% insulin/citrate, 20% insulin-mannitol/citrate and 20% insulin-raffinose/citrate powders, respectively. Animals were fasted overnight.
Figure 3B:
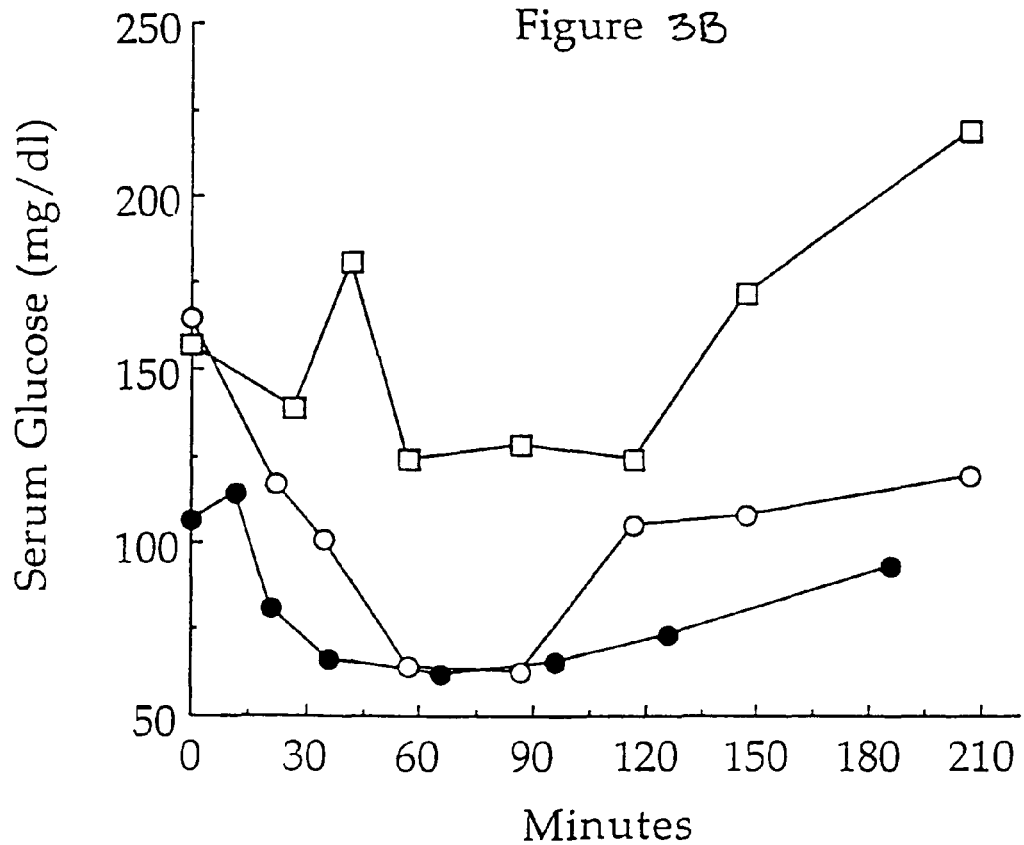

*T's measured from end of aerosol exposure period.
Glucose min = time to >85% of maximal reduction observed in study
**Based on insulin recovered by lavage from lung at end of aerosol exposure
***Based on insulin inhaled, includes losses in nasal passages and throat All three formulations provided rapid absorbing insulin to the rats systemic circulation (FIGS. 3A and 3B). The bioavailability and glucose response were higher for the 20% insulin/mannitol powder (Table 3), although without performing many replicate experiments, it is uncertain if the difference was significant.

Primate Results

Figure 4A:
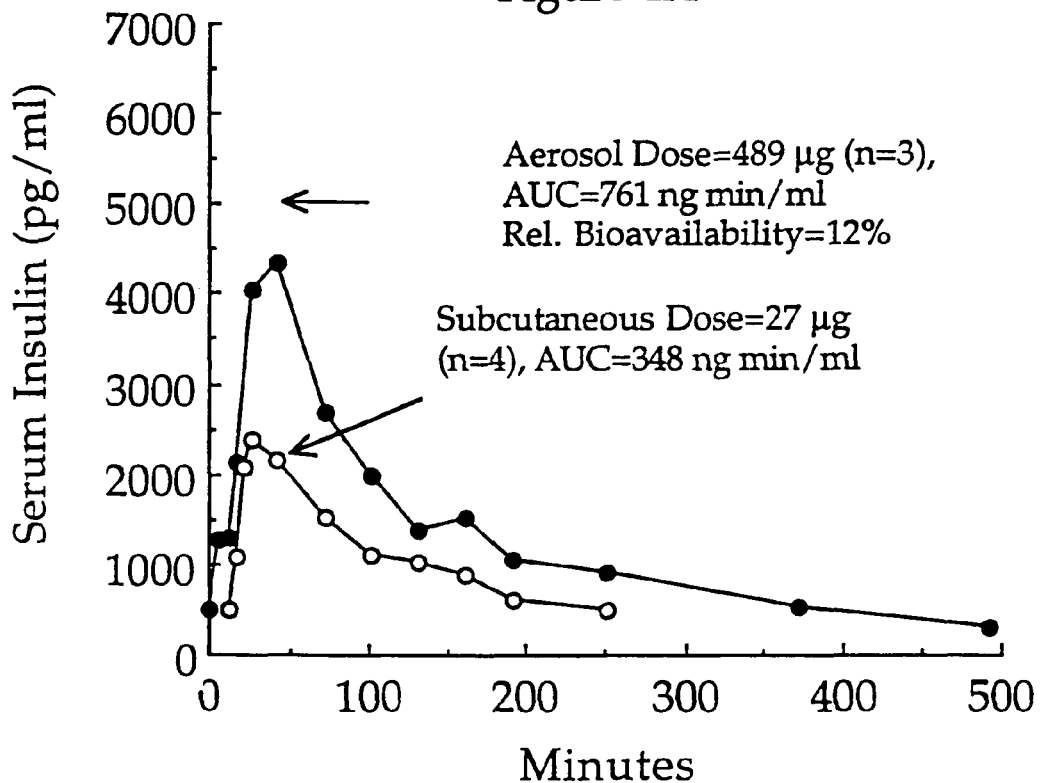
FIGS. 4A and 4B are graphs illustrating mean serum time-concentration insulin and glucose profiles, respectively comparing aerosol and subcutaneous administrations in cynomolgus monkeys. The mean value for three monkeys is reported for the aerosol group, and the mean value for four monkeys is reported for the subcutaneous group.
Figure 4B:
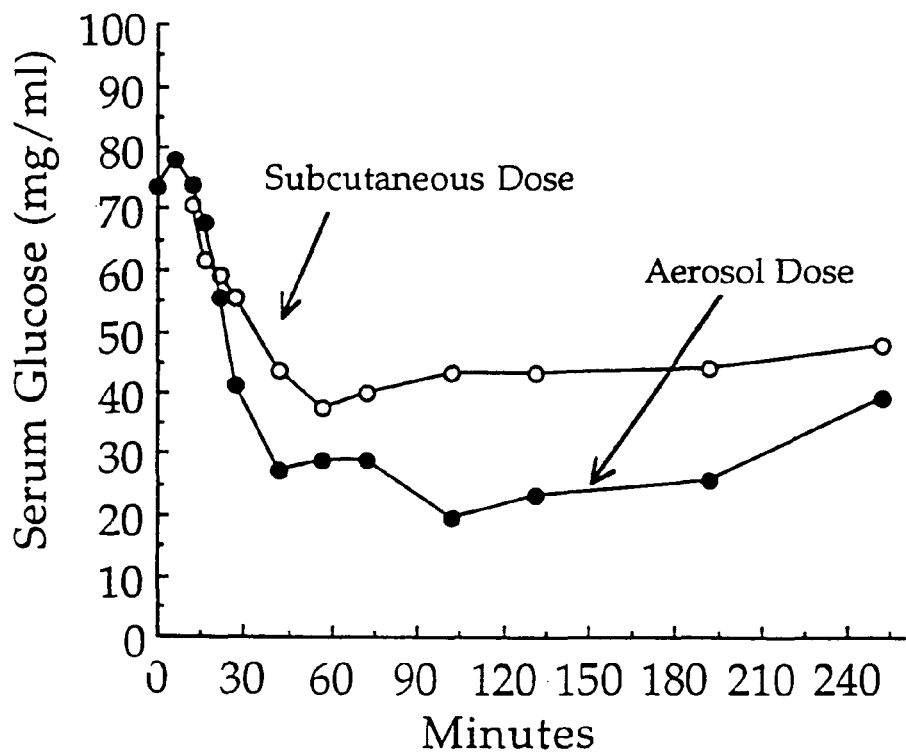

A dose identical to what was used in the human trial (0.2 U/kg, ~27 µg/monkey) was injected into four monkeys to provide the SC data with which to compare the aerosol results (FIGS. 4A and 4B). Table 4 shows the monkey aerosol exposure data. Table 5 shows the mean serum insulins and glucoses for the aerosol exposure and the subcutaneous study. The aerosol dose yielded a robust insulin and glucose response (high dose). FIG. 4 shows a comparison of the mean serum insulin profiles from the two aerosol and one SC study. From the AUCs of these profiles the relative bioavailability of the aerosol insulin was calculated to be 12%.

Human Results

The comparative results between respiratory delivery and subcutaneous injection are set forth in Table 5 below. Respiratory aerosol delivery resulted in more rapid absorption (peak at 20 minutes) than injection (peak at 60 minutes) with a more rapid glucose response (trough at 60 minutes) than with injection (trough at 90 minutes). Reproducibility was as good if not better with aerosol than with injection in both insulin and glucose response. Injection doses were carefully adjusted for weight, aerosol doses were not. Biological activity of aerosol insulin, based on glucose response, relative to injection was 28–36%. Bioavailability of aerosol insulin, based on area-under-the-insulin curve, relative to injection was 22.8% for the 3 puff group.

TABLE 4

Monkey Aerosol Exposure Data

| Animal ID | Grav. filter Mass (mg) | Avg Aerosol Conc. (µg/L) | Inhaled Volume (L) | Est. Inhaled Aerosol Mass (µg) | Est. Inhaled Insulin Mass (µg) | Body Wt. (Kg) | Est. Insulin Dose (µg/kg) | AUC (ng min/ml) |
|---|---|---|---|---|---|---|---|---|
| #1, 23-46 | 1.07 | 178 | 8.96 | 1597 | 320 | 3.92 | 81.5 | 347 |
| #2, 23-48 | 1.01 | 168 | 19.98 | 3363 | 673 | 3.81 | 176.6 | 1196 |
| #3, 122-55 | 0.97 | 162 | 14.68 | 2373 | 475 | 4.1 | 115.7 | 739 |
|  |  |  |  |  | 489 ± 178 |  |  |  |

TABLE 5

Serum Insulin and Glucose Results in Humans

| Subject #s | Dose/Injection or Blister | Dose in Subject* | Increase in Serum Insulin µU/ml | Time of Maximum | Relative Bioavailability Based on Insulin AUC |
|---|---|---|---|---|---|
| INSULIN |  |  |  |  |  |
| 1–24 (SC Injection) | 10.4 U | 10.4 U | 5.8–20.9 | 60 min | 100.0% |
| 7–24 (3 puffs) | 76.0 U | 31.9 U | 6.1–28.5 | 20 min | 22.8% |

TABLE 5-continued

Serum Insulin and Glucose Results in Humans

| Subject #s | Drop in Mean Serum Glucose mg/dl | mg/dl drop | Time of Minimum | % SC | Relative Bioactivity Based on Glucose Drop |
|---|---|---|---|---|---|
| GLUCOSE | | | | | |
| 1–24 (SC Injection) | 93.6–64.9 | 28.7 | 90 min | 100% | 100% |
| 7–24 (3 puffs) | 91.8–67.6 | 24.2 | 60 min | 84.3% | 27.4% |

*Device Eff = 42%

The results of the human trials are further presented in FIGS. 5A–5B. FIG. 5A shows mean serum insulin over time for subcutaneous injection (○), inhalation (3 puffs, ●). Mean serum glucose levels are similarly presented in FIG. 5B. Insulin peaks and glucose troughs are shown in FIGS. 6A and 6B, respectively, while intersubject variability in serum insulin and glucose are presented in FIGS. 7A and 7B, respectively.

In addition, the shallow inspirations (tidal breathing) of the monkeys during the aerosol exposures do not represent the optimal breathing maneuver for deep lung deposition. A higher bioavailability was observed in humans (Table 5), as expected, when the optimum breathing maneuver was used and the aerosol bolus was taken by oral inhalation rather than by nasal inhalation.

Although the foregoing invention has been described in some detail by way of illustration and example, for purposes of clarity of understanding, it will be obvious that certain changes and modifications may be practiced within the scope of the appended claims.

What is claimed is:

1. A method for preparing a dry powder insulin composition, said method comprising:
   dissolving insulin in an aqueous buffer at a concentration in the range from 0.01% to 1% to form a solution; and
   spray drying the solution to produce particles having an average size below 10 μm.

2. A method as in claim 1, wherein the insulin is dissolved in an aqueous buffer together with a pharmaceutical carrier, wherein a dry powder having insulin present in individual particles at from 5% to 99% by weight is produced upon spray drying.

3. A method as in claim 2, wherein the pharmaceutical carrier is a carbohydrate, organic salt, amino acid, peptide, or protein which produces a powder upon spray drying.

4. A method as in claim 3, wherein the pharmaceutical carrier is a carbohydrate selected from the group consisting of mannitol, raffinose, lactose, maltodextrin and trehalose.

5. A method as in claim 2, wherein the pharmaceutical carrier is an organic salt selected from the group consisting of sodium citrate, sodium acetate, and sodium ascorbate.

6. An insulin composition for pulmonary delivery, said composition comprising a dry powder of individual particles which include insulin present at from 20% to 80% by weight in a pharmaceutical carrier material, wherein the particles have an average size below 10 μm.

7. An insulin composition as in claim 6, wherein the composition is substantially free from penetration enhancers.

8. An insulin composition as in claim 6, wherein the pharmaceutical carrier material comprises a carbohydrate selected from the group consisting of mannitol, raffinose, lactose, maltodextrin, and trehalose.

9. An insulin composition as in claim 6, wherein the pharmaceutical carrier material comprises an organic salt selected from the group consisting of sodium citrate, sodium gluconate, and sodium ascorbate.

10. A method for preparing a dry powder insulin composition, said method comprising:
    providing an aqueous solution of insulin and a pharmaceutical carrier dissolved in an aqueous buffer, wherein the insulin is present at 0.01% to 1% by weight and comprises from 20% to 80% of the total weight of insulin and pharmaceutical carrier in the solution; and
    spray drying the solution to produce particles comprising both the insulin and the pharmaceutical carrier having an average size below 10μm and a moisture content below 10%.

11. A method as in claim 10, wherein the pharmaceutical carrier is a carbohydrate, organic salt, amino acid, peptide, or protein which produces a powder upon spray drying.

12. A method as in claim 11, wherein the carbohydrate carrier is selected from the group consisting of mannitol, raffinose, lactose, maltodextrin and trehalose.

13. A method as in claim 10, wherein the carrier is an organic salt selected from the group consisting of sodium citrate, sodium acetate, and sodium ascorbate.

14. An insulin composition for pulmonary delivery, said composition comprising:
    a dry powder of individual particles including both insulin and a pharmaceutical carrier, wherein the particles comprise from 20% to 80% insulin by weight, have an average particle size below 10μm, and have a moisture content below 10%.

15. An insulin composition as in claim 14, wherein the particles consist essentially of the insulin and the pharmaceutical carrier.

16. An insulin composition as in claim 14, wherein the composition is substantially free from penetration enhancers.

17. An insulin composition as in claim 14, wherein the pharmaceutical carrier comprises a carbohydrate selected from the group consisting of mannitol, raffinose, lactose, maltodextrin, and trehalose.

18. An insulin composition as in claim 14, wherein the pharmaceutical carrier comprises an organic salt selected from the group consisting of sodium citrate, sodium gluconate, and sodium ascorbate.

19. A method as in claim 1, wherein the composition is substantially free from penetration enhancers.

20. A method as in claim 1, wherein the particles are substantially amorphous.

21. A composition as in claim 6, wherein the composition is substantially amorphous.

22. A method as in claim 10, wherein the particles have a moisture content less than about 5% by weight.

23. A method as in claim 10, wherein the particles are substantially amorphous.

24. An insulin composition as in claim 14, wherein the particles have a moisture content less than about 5% by weight.

25. An insulin composition as in claim 14, wherein the particles are substantially amorphous.

26. An insulin composition for pulmonary delivery, said composition comprising a dry powder of individual particles including insulin present at from 5% to 80% by weight in a pharmaceutical carrier material, wherein the particles have an average size below 10 μm.

27. An insulin composition as in claim 26, wherein the composition is substantially free from penetration enhancers.

28. An insulin composition as in claim 26, wherein the pharmaceutical carrier material comprises a carbohydrate selected from the group consisting of mannitol, raffinose, lactose, maltodextrin, and trehalose.

29. A composition as in claim 26, wherein the composition is substantially amorphous.

30. A composition as in claim 26, wherein the particles have a moisture content less than about 10% by weight.

31. A composition as in claim 26, wherein the particles have a moisture content less than about 5% by weight.

32. A method for preparing a dry powder insulin composition, said method comprising:

providing an aqueous solution of insulin and a pharmaceutical carrier dissolved in an aqueous buffer, wherein the insulin is present at 0.01% to 1% by weight and comprises from 5% to 80% of the total weight of insulin and pharmaceutical carrier in the solution; and spray drying the solution to produce particles comprising both the insulin and the pharmaceutical carrier having an average size below 10 μm and a moisture content below 10%.

33. A method as in claim 32, wherein the particles have a moisture content less than about 5% by weight.

34. A method as in claim 32, wherein the particles are substantially amorphous.

* * * * *